US006235727B1

(12) United States Patent
Schudok et al.

(10) Patent No.: US 6,235,727 B1
(45) Date of Patent: May 22, 2001

(54) SULFONYLAMINOPHOSPHINIC AND SULFONYLAMINOPHOSPHINIC ACID DERIVATIVES, METHODS FOR THEIR PREPARATION AND USE

(75) Inventors: Manfred Schudok, Eppstein; Wilfried Schwab, Wiesbaden; Gerhard Zoller, Schöneck; Eckart Bartnik, Wiesbaden-Delkenheim; Frank Büttner, Ludwigshafen; Klaus-Ulrich Weithmann, Hofheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/353,086

(22) Filed: Jul. 15, 1999

(30) Foreign Application Priority Data

Jul. 16, 1998 (DE) .............................. 198 31 980
May 12, 1999 (DE) .............................. 199 21 680

(51) Int. Cl.$^7$ ................ C07F 9/38; C07F 9/40; C07F 9/572; A61K 31/66

(52) U.S. Cl. ................ 514/80; 514/91; 514/117; 514/125; 514/128; 548/413; 548/414; 558/169; 558/170; 568/15; 568/16; 568/17

(58) Field of Search .................. 514/125, 128, 514/80, 91, 117; 423/302, 303, 317; 568/15, 17; 548/413, 414; 558/169, 170; 562/15, 16, 17

(56) References Cited

U.S. PATENT DOCUMENTS

| | | | |
|---|---|---|---|
| 3,996,040 | * 12/1976 | Franz | 71/87 |
| 4,755,209 | * 7/1988 | Azuma et al. | 71/86 |
| 4,859,602 | * 8/1989 | Zimmermann et al. | 435/280 |
| 5,453,537 | * 9/1995 | Morikawa et al. | 562/17 |

FOREIGN PATENT DOCUMENTS

| | | |
|---|---|---|
| 64823/98 | 11/1998 | (AU) . |
| 64824/98 | 11/1998 | (AU) . |
| 0 243 173 A2 | 10/1987 | (EP) . |
| 0 305 947 B1 | 3/1989 | (EP) . |
| 0 468 231 B1 | 1/1992 | (EP) . |
| 0 606 046 A1 | 7/1994 | (EP) . |
| 0 757 037 A2 | 2/1997 | (EP) . |
| 0 877 018 A1 | 11/1998 | (EP) . |
| 0 877 019 A1 | 11/1998 | (EP) . |
| WO 95/35276 | 12/1995 | (WO) . |
| WO 96/27583 | 9/1996 | (WO) . |
| WO 97/44315 | 11/1997 | (WO) . |
| 98/32738 | * 7/1998 | (WO) . |
| WO 98/50348 | * 11/1998 | (WO) . |

OTHER PUBLICATIONS

Okubo et al., Chem. Abstract 127:220580, 1997.*
Kitamura et al., Chem. Abstract 126:199805, 1997.*
Courture et al., Chem. Abstract 126:19077, 1996.*
Hashem et al., Chem. Abstract 102:166837, 1985.*
Bassin, J.P., et al., "Chlorosulfonation of Some Polynuclear Heterocyclic Compounds," *Phosphorus, Sulfur, and Silicon*, 1992, 72:157–170.
Büttner, F.H., et al., "Expression of Membrane Type 1 Matrix Metalloproteinase in Human Articular Cartilage," *Arthritis & Rheumatism*, 1997, 40:4:704–709.
Büttner, F.H., et al., "Membrane type 1 matrix metaloproteinase (MT1–MMP) cleaves the recombinant aggrecan substrate rAgg1$_{mut}$ at the 'aggrecanase' and the MMP sites," *Biochem. J.*, 1998, 333:159–165.
Fosang, A.J., et al., "Aggrecan Is Degraded by Matrix Metalloproteinases in Human Arthritis," *J. Clin. Invest.*, 1996, 98:10:2292–2299.
Genêt, J.P., et al., "Practical Synthesis of α–Aminophosphonic Acids," *Tetrahedron Letters*, 1992, 33:1:77–80.
Giannousis, P.P., et al., "Phosphorus Amino Acid Analogues as Inhibitors of Leucine Aminopeptidase," *J. Med. Chem.*, 1987, 30:1603–1609.
Hughes, C.E., et al., "Monoclonal antibodies that specifically recognize neoepitope sequences generated by 'aggrecanase' and matrix metalloproteinase cleavage of aggrecan: application to catabolism in situ and in vitro," *Biochem. J.*, 1995, 305:799–804.
Hughes, C.E., et al., "Utilization of a Recombinant Substrate rAgg1 to Study the Biochemical Properties of Aggrecanase in Cell Culture Systems," *The Journal of Biological Chemistry*, 1997, 272:32:20269–20274.
Lark, M.W., et al., "Cell–mediated Catabolism of Aggrecan," *The Journal of Biological Chemistry*, 1995, 270:6:2550–2556.
Lohmander, L.S., et al., "The Structure of Aggrecan Fragments in Human Synovial Fluid," *Arthritis & Rheumatism*, 1993, 36:9:1214–1222.

(List continued on next page.)

Primary Examiner—Mukund J. Shah
Assistant Examiner—Deepak R. Rao
(74) Attorney, Agent, or Firm—Finnegan, Henderson, Farabow, Garrett and Dunner, L.L.P.

(57) ABSTRACT

Compounds of the formula I

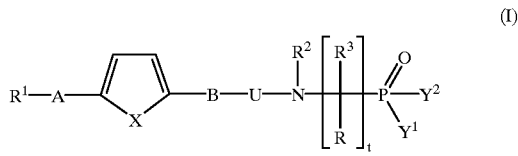

(I)

are suitable for the production of pharmaceuticals for the prophylaxis and therapy of disorders in the course of which an increased activity of matrix-degrading enzymes is involved.

22 Claims, No Drawings

OTHER PUBLICATIONS

Roemmel. R.C., et al., "Removal of N–Arylsulfonyl Groups from Hydroxy α–Amino Acids," *J. Org. Chem.*, 1988, 53:2367–2371.

Rogers, R.S., et al., "An Improved Synthesis of the Phosphonic Acid Analog of Tryptophan," *Synlett*, 1992, pp. 708–709.

Suter, C.M., "Studies in the Diphenyl Ether Series. II. Preparation and Structure of Some Sulfonic Acids and Related Derivatives," *J. Am. Chem. Soc.*, 1931, 53:1112–1116.

Ye, Q., et al., "Purification and Characterization of the Human Stromelysin Catalytic Domain Expressed in *Escherichia coli*," *Biochemistry*, 1992, 31:11231–11235.

* cited by examiner

SULFONYLAMINOPHOSPHINIC AND SULFONYLAMINOPHOSPHINIC ACID DERIVATIVES, METHODS FOR THEIR PREPARATION AND USE

The invention relates to novel sulfonylaminophosphinic and sulphonylaminophosphonic acid derivatives, processes for their preparation and use thereof as pharmaceuticals.

The present application claims priority under 35 U.S.C. § 119 to German applications No. 19831980.0 filed Jul. 16, 1998, and No. 19921680.0 filed May 12, 1999. Both priority applications are entirely incorporated herein by reference.

The applications EP 0 606 046, WO 95/35276 and WO 96/27583 describe arylsulfonamidohydroxamic acids and their action as matrix metalloproteinase inhibitors. Specific arylsulfonamidocarboxylic acids are used as intermediates for the preparation of thrombin inhibitors (EP 0 468 231) and aldose reductase inhibitors (EP 0 305947). The application EP 0757 037 also describes the action of sulfonylaminocarboxylic acid derivatives as metalloproteinase inhibitors. The arylsulfonyl group has furthermore proved to be an effective protective group of the amino function of α-aminocarboxylic acids. R. Roemmele, H. Rapoport, 53 J. ORG. CHEM. 2367 (1988).

In the attempt to find efficacious compounds for the treatment of connective tissue disorders, it has now been found that the sulfonylaminophosphinic and -phosphonic acid derivatives according to the invention are strong inhibitors of metalloproteinases. Particular value is placed here on the inhibition of stromelysin (matrix metalloproteinase 3, "MMP-3"), of neutrophil collagenase ("MMP-8") and of aggrecanase, since these enzymes are involved to a considerable extent in the degradation of proteoglycans, as important constituents of the cartilaginous tissue. A. J. Fosang et al., 98 J. CLIN. INVEST. 2292 (1996).

The pathological loss of aggrecan, the main proteoglycan of the cartilage, includes proteolytic cleavages in its interglobular domain. Amino acid sequence analyses of proteoglycan metabolites, isolated from the synovial fluid of patients who are suffering from injury to a joint, from osteoarthrosis or from an inflammatory joint condition, showed that a proteolytic cleavage preferably takes place between the amino acids Glu$^{373}$ and Ala$^{374}$ in the interglobular domain of human aggrecan. Lohmander et al., 36 ARTHRITIS RHEUM. 1214 (1993). Until now, it was not yet possible to identify the proteolytic activity which is responsible for this cleavage. It is designated as "aggrecanase" and can be included in the metalloproteinases family.

The detection of the expression of MT1-MMP in human cartilaginous tissue for the first time (Büttner et al., 40 ARTHRITIS RHEUM. 704 (1997)), combined with the proof that the catalytic domain of this enzyme cleaves at the "aggrecanase" cleavage site in the recombinant aggrecan fusion protein rAgg1$_{mut}$ (Büttner et al., 333 BIOCHEM. J. 159 (1998)), led to the testing of the strong matrix metalloproteinase inhibitors described here with respect to their action against an "aggrecanase" activity. It was possible here to show using various assay systems that the sulfonylaminophosphinic and -phosphonic acid derivatives are also strong inhibitors for the "aggrecanase" activity.

The invention therefore relates to the compounds of the formula I

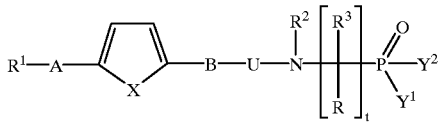

(I)

stereoisomeric forms thereof, and physiologically tolerable salts thereof, where (A.) $R^1$ is
1. phenyl;
2. phenyl, which is mono- or disubstituted by
   2.1. ($C_1$–$C_6$)alkyl,
   2.2. hydroxyl,
   2.3. ($C_1$–$C_6$)-alkyl-C(O)—O—,
   2.4. ($C_1$–$C_6$)-alkyl-O—,
   2.5. ($C_1$–$C_6$)-alkyl-O-($C_1$–$C_4$)-alkyl-O—,
   2.6. halogen,
   2.7. —$CF_3$,
   2.8. —CN,
   2.9. —$NO_2$,
   2.10. HO—C(O)—,
   2.11. ($C_1$–$C_6$)-alkyl-O—C(O)—,
   2.12. methylenedioxo,
   2.13. $R^4$—($R^5$)N—C(O)—,
   2.14. $R^4$—($R^5$)N—, or
   2.15 a heteroaromatic described under A.3.1 to A.3.16;
3. a heteroaromatic described under A.3.1 to A.3.16, which is unsubstituted or substituted by one or more radicals described under A.2.1 to A.2.15,
   3.1. pyrrole,
   3.2. pyrazole,
   3.3. imidazole,
   3.4. triazole,
   3.5. thiophene,
   3.6. thiazole,
   3.7. oxazole,
   3.8. isoxazole,
   3.9. pyridine,
   3.10. pyrimidine,
   3.11. pyrrolidine,
   3.12. indole,
   3.13. benzothiophene,
   3.14. benzimidazole,
   3.15. benzoxazole, or
   3.16. benzothiazole; or
4. —O-($C_1$–$C_6$)-alkyl;

(B.) $R^2$, $R^4$ and $R^5$ independently of one another are identical or different and are
1. a hydrogen atom;
2. ($C_1$–$C_6$)-alkyl-;
3. HO—C(O)-($C_1$–$C_6$)-alkyl-;
4. phenyl-($CH_2$)$_n$—, in which phenyl is unsubstituted or mono- or disubstituted with radicals described under A.2.1 to A.2.15, or is substituted by —NH—C(O)-($C_1$–$C_3$)-alkyl, and n is the integer zero, 1, or 2;
5. picolyl; or
6. $R^4$ and $R^5$, together with the nitrogen to which they are bonded, form a 4- to 7-membered ring, and the ring is unsubstituted, or a carbon atom in the ring is replaced by —O—, —S—, or —NH—, or two adjacent carbon atoms of the 4- to 7-membered ring are part of a benzyl radical;

(C.) R and R³ are identical or different and are
1. a hydrogen atom;
2. (C₁–C₁₀)-alkyl-, in which alkyl is unsubstituted or monosubstituted by —OH;
3. (C₂–C₁₀)-alkenyl-, in which alkenyl is linear or branched;
4. R²—O-(C₁–C₆)-alkyl-;
5. R²—S(O)ₙ-(C₁–C₆)-alkyl-, where n is the integer zero, 1, or 2;
6. R²—S(O)(=NH)-(C₁–C₆)-alkyl-;
7. a radical of formula IIo

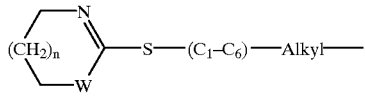

(IIo)

in which n is the integer zero, 1, or 2, and W is a nitrogen, oxygen, or sulfur atom;
8. phenyl-(CH₂)ₘ—, in which m is the integer zero, 1, 2, 3, 4, 5, or 6, wherein the —(CH₂)ₘ— chain is unsubstituted or monosubstituted by —OH, and wherein phenyl is unsubstituted or mono- or disubstituted by
  8.1 radicals described under A.2.1 to A.2.15,
  8.2 —O—(CH₂)ₘ-phenyl, in which phenyl is unsubstituted or mono- or disubstituted with radicals described under A.2.1 to A.2.15, and m is the integer zero, 1, 2, 3, 4, 5, or 6,
  8.3 —C(O)-(CH₂)ₘ-phenyl, in which phenyl is defined under C.8.2;
9. heteroaryl-(CH₂)ₘ—, in which heteroaryl is defined under A.3.1 to A.3.16, m is defined under C.8, the —(CH₂)ₘ— chain is unsubstituted or monosubstituted by —OH, and heteroaryl is unsubstituted or mono- or disubstituted by
  9.1 radicals described under A.2.1 to A.2.15,
  9.2 —CH(O),
  9.3 —SO₂-phenyl, in which phenyl is unsubstituted or substituted as defined under C.8.2 or C.8.3,
  9.4 —O—(CH₂)ₘ-phenyl;
10. —(CH₂)ₘ—P(O)(OH)-(C₁–C₃)-alkyl, in which m is defined under C.8;
11. a characteristic radical of an amino acid;
12. R⁶—C(O)-(C₀–C₆)-alkyl- in which R⁶ is
  12.1. a hydrogen atom,
  12.2. (C₁–C₆)-alkyl-,
  12.3. phenyl, which is unsubstituted or substituted with one or more radicals described under A.2.1 to A.2.15,
  12.4. heteroaryl, which is defined under A.3.1 to A.3.16, and is unsubstituted or substituted with one or more radicals described under A.2.1 to A.2.15, or is substituted by -(C₁–C₄)-alkyl-COOH,
  12.5. —OH,
  12.6. —OR², in which R² has the meaning described under B.1 to B.6,
  12.7. —NR⁴—(R⁵), in which R⁴ and R⁵ are defined under B.1 to B.6,
  12.8. heteroaryl-(CH₂)ₘ—NH—, in which heteroaryl is defined under A.3.1 to A.3.16, and is unsubstituted or substituted with one or more radicals described under A.2.1 to A.2.15, and m is defined under C.8,
  12.9. R⁴—(R⁵)N—NH—, in which R⁴ and R⁵ are defined under B.1 to B.6,
  12.10. HO—C(O)—CH(R³)—NH—, in which R³ is defined under C.1 to C.11;
13. —(CH₂)ₚ—N(R⁹)(R¹⁰), in which p is an integer zero, 1, 2, 3, or 4, in which R⁹ and R¹⁰ are identical or different and are
  13.1. a hydrogen atom,
  13.2. phenyl-(CH₂)ₘ—, in which phenyl is unsubstituted or mono- or disubstituted with radicals described under A.2.1 to A.2.15, and m is the integer zero, 1, 2, or 3,
  13.3. Rˣ—C(O)—, in which Rˣ is
    3.1 (C₁–C₆)-alkyl-,
    3.2 (C₂–C₆)-alkenyl-,
    3.3 phenyl-(CH₂)ₘ—, in which phenyl is unsubstituted or mono- or disubstituted with radicals described under A.2.1 to A.2.15, and m is the integer zero, 1, 2, or 3, or
    3.4 heteroaryl-(CH₂)ₘ—, in which heteroaryl is defined under A.3.1 to A.3.16,
  13.4. Rˣ—O—C(O)—, in which Rˣ is defined under C.13.3,
  13.5. Rˣ—CH(NH₂)—C(O)—, in which Rˣ is defined under C.13.3,
  13.6. R⁸—N(R⁷)—C(O)—, in which R⁸ is
    6.1 a hydrogen atom
    6.2 (C₁–C₆)-alkyl-,
    6.3 phenyl-(CH₂)ₘ, in which phenyl is unsubstituted or mono- or disubstituted with radicals described under A.2.1 to A.2.15, and m is the integer zero, 1, 2, or 3, or
    6.4 heteroaryl-(CH₂)ₘ, in which heteroaryl is defined under A.3.1 to A.3.16, and is unsubstituted or substituted with one or more radicals described under A.2.1 to A.2.15, m is the integer zero, 1, 2, or 3, and in which R⁷ is a hydrogen atom or (C₁–C₆)-alkyl-, or in which R⁷ and R⁸, together with the nitrogen atom to which they are bonded, form a 4- to 7-membered ring, and the ring is unsubstituted or a carbon atom in the ring is replaced by —O—, —S—, or —NH—,
  13.7. Rˣ—SO₂—, in which Rˣ is defined under C.13.3,
  13.8. Rˣ—NH—C(=NR⁷)—, in which Rˣ is defined under C.13.3 and R⁷ is defined under C.13.6.4, or Rˣ and R⁷ are
    8.1 (C₁–C₆)-alkyl-C(O)—,
    8.2 —NO₂ or
    8.3 —SO₂—(CH₂)q-phenyl, in which phenyl is unsubstituted or mono- or disubstituted with radicals described under A.2.1 to A.2.15, and q is the integer zero, 1, 2, or 3,
  13.9. —SO₂—(CH₂)q-phenyl-phenyl, in which each phenyl independently is unsubstituted or mono- or disubstituted with radicals described under A.2.1 to A.2.15, and q is the integer zero, 1, 2, or 3, or
  13.10. a radical of formula IIp

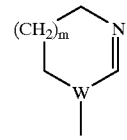

(IIp)

in which m is the integer zero, 1, 2, or 3, and W is a nitrogen atom or sulfur atom, or $R^9$ and $R^{10}$, together with the nitrogen atom to which they are bonded, form a ring chosen from radicals of the subformulae IIa to IIn,

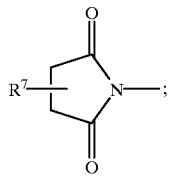
(IIa)

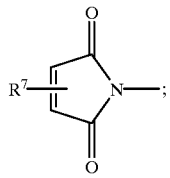
(IIb)

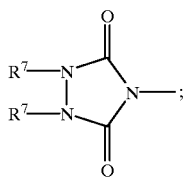
(IIc)

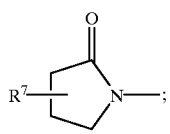
(IId)

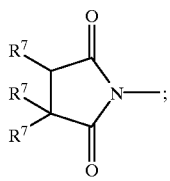
(IIe)

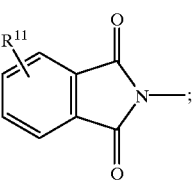
(IIf)

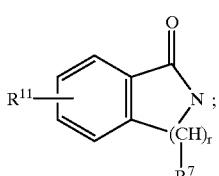
(IIg)

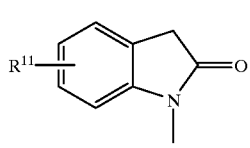
(IIh)

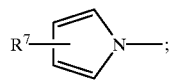
(IIi)

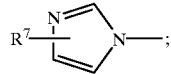
(IIj)

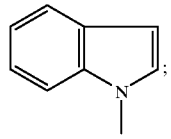
(IIk)

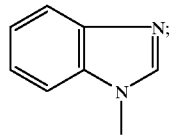
(IIl)

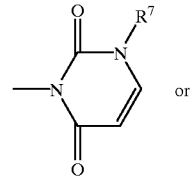
(IIm)

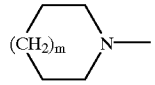
(IIn)

where r is the integer 1 or 2, $R^{11}$ is a radical described under A.2.1 to A.2.15, $R^7$ is defined under C.13.6.4, and m is defined under C.13.2, and a carbon atom in the ring is replaced by zero or one heterospecies chosen from oxygen, sulfur, or nitrogen atom which is unsubstituted or monosubstituted with $R^2$;

14. —OH;
15. =O;
16. $(C_1–C_6)$-alkyl; or in the compound of formula I, a —C(R)(R$^3$)— radical is optionally replaced by —NH— or —NR$^2$— in which $R^2$ is defined under B.1 to B.6;

(D.) t is an integer 1, 2, 3, or 4;

(E.) $R^2$ and $R^3$ together form a ring with an exocyclic phosphinic or phosphonic acid radical of the subformula II

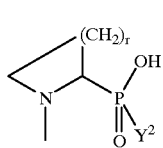
(II)

in which r is the integer zero, 1, 2, or 3, and one carbon atom in the ring of the radical of subformula II is replaced by zero or one heterospecies chosen from —O—, —S—, or —(R$^7$)N—, in which $R^7$ is 1. a hydrogen atom;
2. $(C_1–C_6)$-alkyl;

3. phenyl, in which phenyl is unsubstituted or substituted with one or more radicals described under A.2.1 to A.2.15;
4. benzyl, in which benzyl is unsubstituted or substituted with one or more radicals described under A.2.1 to A.2.15; or
5. $R^2N—C(=NH)—$ where $R^2$ has the meaning described under B.1 to B.6, and the carbon atoms in the ring of the subformula II are unsubstituted or mono- or polysubstituted by $(C_1–C_6)$-alkyl-, phenyl-, phenyl-$(CH_2)_m$— or HO—, or combinations thereof;

(F.) U is —$SO_2$— or —CO—;
(G.) $Y^1$ and $Y^2$ are identical or different and independently of one another are
  a) a hydrogen atom;
  b) —OH;
  c) —$(C_1–C_4)$-alkyl, in which alkyl is linear or branched;
  d) —$(CH_2)_u$-phenyl, in which u is zero or 1;
  e) —O-$(C_1–C_4)$-alkyl, in which alkyl is linear or branched; or
  f) —O-$(CH_2)_s$-phenyl, in which s is zero or 1;
(H.) A is
  a) a covalent bond;
  b) —O—;
  c) —CH=CH—; or
  d) —C≡C—;
(I.) B is
  a) —$(CH_2)_m$—, in which m is defined under C.13.2;
  b) —O—$(CH_2)_p$, in which p is an integer from 1 to 5; or
  c) —CH=CH—; and
(J.) X is —CH=CH—, an oxygen atom, or a sulfur atom.

A preferred compound of the formula I is one where $R^1$ is
  1. phenyl;
  2. phenyl which is monosubstituted by
    2.1. $(C_1–C_6)$-alkyl-,
    2.2. —OH,
    2.3. —C(O)—OH,
    2.4. —O-$(C_1–C_6)$-alkyl,
    2.5. pyrrolidone,
    2.6. halogen, or
    2.7. —$CF_3$; or
  3. —O-$(C_1–C_6)$-alkyl;
$R^2$, $R^4$ and $R^5$ are identical or different and are a hydrogen atom or $(C_1–C_6)$-alkyl-;
R is a hydrogen atom;
$R^3$ is
  1. $(C_1–C_6)$-alkyl-, in which alkyl is unsubstituted or monosubstituted by —OH,
  2. $R^2$—S(O)$_n$-$(C_1–C_6)$-alkyl-, in which $R^2$ is $(C_1–C_6)$-alkyl- or phenyl-$(CH_2)_n$—, and n is the integer zero or 1;
  3. —$(CH_2)_m$-phenyl, in which phenyl is unsubstituted or mono- or disubstituted with radicals described under A.2.1 to A.2.15 in the original definition of the compound of formula I, the —$(CH_2)_m$— chain is unsubstituted or monosubstituted by —OH, and m is the integer 1, 2, 3, 4, or 5;
  4. —$(CH_2)_m$-heteroaryl, in which heteroaryl has the meaning mentioned under A.3.3, A.3.5, A.3.6, A.3.9, or A.3.11 in the original definition of the compound of formula I, and is unsubstituted or substituted with one or more radicals described under A.2.1 to A.2.15 in the original definition of the compound of formula I, the —$(CH_2)_m$— chain is unsubstituted or monosubstituted by —OH, and m is the integer 1, 2, 3, or 4;
  5. a characteristic radical of an amino acid;
  6. —$(CH_2)_p$—N($R^9$)($R^{10}$), in which p is the integer zero, 1, or 2 in which $R^9$ and $R^{10}$ are identical or different and are a hydrogen atom or —$SO_2$—$(CH_2)_q$-phenyl-phenyl, in which each phenyl independently is unsubstituted or mono- or disubstituted with radicals described under A.2.1 to A.2.15 in the original definition of the compound of formula I, and q is the integer zero, 1, 2, or 3; or
  7. $R^6$—C(O)—, in which $R^6$ is
    7.1. —OH,
    7.2. $R^2$O—, in which $R^2$ is defined under B.1 to B.6 in the original definition of the compound of formula I, or
    7.3. $R^4$—($R^5$)N—, in which $R^4$ and $R^5$ are defined under B.1 to B.6 in the original definition of the compound of formula I;
  8. a hydrogen atom;
  9. —OH;
  10. =O; or
  11. $(C_1–C_6)$-alkyl-; or
in the compound of formula I, a —C(R)($R^3$)— radical is optionally replaced by —NH— or —$NR^2$—, in which $R^2$ is defined under B.1 to B.6 in the original definition of the compound of formula I; and
  t is an integer 1, 2, 3, or 4;
  U is —$SO_2$—;
  $Y^1$ is —OH;
  $Y^2$ is a) —O-$(C_1–C_4)$-alkyl, in which alkyl is linear or branched,
    b) —OH, or
    c) -$(C_1–C_4)$-alkyl, in which alkyl is linear or branched;
  A is a covalent bond or —O—;
  B is a covalent bond or -$(C_1–C_4)$-alkyl; and
  X is —CH=CH—.

A particularly preferred compound of the formula I is one where
  $R^1$ is phenyl which is monosubstituted by halogen;
  $R^2$ is a hydrogen atom;
  R is a hydrogen atom;
  $R^3$ is
    1. $(C_1–C_4)$-alkyl-;
    2. -phenyl, in which phenyl is unsubstituted or mono- or disubstituted by —$CF_3$ or —COOH;
    3. a hydrogen atom;
    4. —OH; or
    5. —NH—$SO_2$-phenyl-phenyl, in which each phenyl independently is unsubstituted or substituted by one ore more identical or different halogen atoms;
  t is an integer 1, 2, 3, or 4;
  U is —$SO_2$—;
  $Y^1$ and $Y^2$ are identical or different and are —OH or —O—$CH_3$;
  A is a covalent bond;
  B is a covalent bond or —$(CH_2)_o$—, in which o is 1, 2, or 3; and
  X is CH=CH—.

Particularly preferred compounds are (R)-[1-(4'-chlorobiphenyl-4-sulfonyl-amino)-2-methylpropyl] phosphonic acid, dimethyl [3-(4'-chlorobiphenyl-4-sulfonylamino)-1-hydroxy-3-(4-trifluoromethylphenyl)

propyl]phosphonate, [1-(4'-chlorobiphenyl-4-sulfonylamino)-3-methylbutyl]phosphonic acid, stereoisomeric forms thereof, and physiologically tolerable salts of any of the foregoing.

The expression "$R^4$ and $R^5$ together with the ring amino group form a 4- to 7-membered ring and/or one of the carbon atoms is replaced by —O—, —S— or —NH—" is understood as meaning radicals which are derived, for example, from azetidine, pyrrole, pyrroline, pyridine, azepine, piperidine, oxazole, isoxazole, imidazole, indoline, pyrazole, thiazole, isothiazole, diazepine, thiomorpholine, pyrimidine or pyrazine. The term "halogen" is understood as meaning fluorine, chlorine, bromine or iodine. The term "alkyl" or "alkenyl" is understood as meaning hydrocarbon radicals whose hydrocarbon chains are linear, branched, or cyclic, unless otherwise indicated. Cyclic alkyl radicals are, for example, 3- to 6-membered monocydic systems such as cyclopropyl, cyclobutyl, cyclopentyl or cyclohexyl. The alkenyl radicals can furthermore also contain a number of double bonds.

When a radical is multisubstituted with other radicals, said other radicals are understood to be independently chosen, being identical or different from each other. For example, in the phrase "a heteroaromatic . . . which is unsubstituted or substituted by one or more radicals described under A.2.1 to A. 2.15," it is intended that said radicals may be mixed and matched, with the identity of one radical having no bearing on the identity of another. Similarly, when a radical is disubstituted with other radicals, said other radicals are identical or different.

The general structural formula of α-amino acids is as follows:

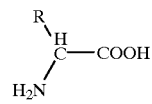

α-amino acids differ from one another by the radical R, which in the context of the present application is designated as a "characteristic radical" of an amino acid.

The starting substances for the chemical reactions are known or can be easily prepared by methods known from the literature. The aminophosphinic and -phosphonic acids used as starting substances for the synthesis of the compounds according to the invention are, if not commerically obtainable in the individual case, synthesizable according to known methods (R. S. Rogers, M. K. Stem, SYNLETT, 708 (1992); P. P. Giannousis, P. A. Bartlett, 30 J. MED. CHEM. 1603 (1987); J. P. Genet, M. Uziel, A. M. Touzin, S. Roland, S. Thorimbert, S. Tanier, 33 TETRAHEDRON LETT. 77 (1992); E. K. Baylis, C. D. Campbell, J. G. Dingwall, 1 J. CHEM. SOC. PERKIN TRANS. 2845 (1984)).

The invention furthermore relates to a process for the preparation of the compounds of the formula I and/or a stereoisomeric form of the compounds of the formula I and/or of a physiologically tolerable salt of the compounds of the formula I, which comprises a) reacting an aminophosphinic or -phosphonic acid of the formula III

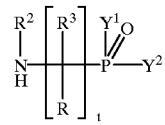

(III)

in which $R^2$, $Y^1$, $Y^2$, R, and $R^3$ are as defined in formula I, with a sulfonic acid or carbonyl derivative of the formula IV

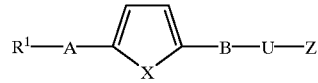

(IV)

in which $R^1$, A, X, U, and B are as defined in formula I and Z is a halogen atom, imidazolyl or —$OR^8$, in which $R^8$ is a hydrogen atom, ($C_1$–$C_6$)-alkyl, phenyl or benzyl, wherein said alkyl, phenyl, or benzyl is independently unsubstituted or substituted, in the presence of a base or optionally of a dehydrating agent to give a compound of the formula I, or b) reacting an aminophosphinic or -phosphonic acid ester of the formula (V)

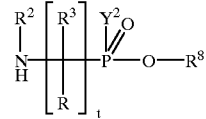

(V)

in which $R^2$, $R^3$, t, $Y^2$ and $R^8$ have the abovementioned meaning, with a sulfonic acid or carbonyl derivative of the formula IV to give a compound of the formula VI

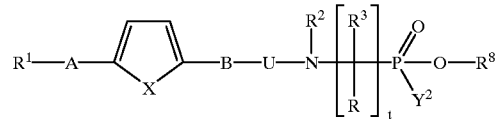

(VI)

and converting the compound of the formula VI with removal of the radical $R^8$, preferably in the presence of a base or acid, into a compound of the formula I, or c) reacting the compound of the formula VII

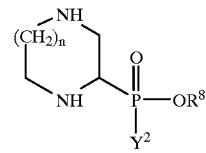

(VII)

where n is the integer zero, 1 or 2, with the aid of a protective group E to give a compound of the formula VIII

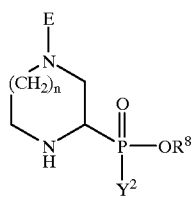

(VIII)

and converting the compound of the formula VIII, using a compound of the formula IV into a compound of the formula IX

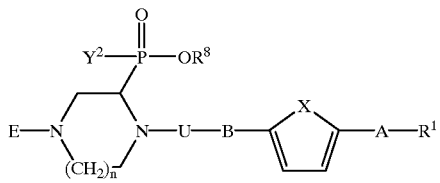

(IX)

and then converting the compound of the formula IX, with removal of the protective group E and of the radical $R^8$ with the aid of suitable cleavage reagents, into the compound of the formula I, or d) separating a compound of the formula I prepared by one of the processes a), b) or c), which on account of its chemical structure occurs in enantiomeric forms, into the pure enantiomers by salt formation with enantiomerically pure acids or bases, chromatography on chiral stationary phases or dervatization by means of chiral enantiomerically pure compounds such as amino acids, separation of the diastereomers thus obtained, and removal of the chiral auxiliary groups, or e) isolating the compound of the formula I prepared by one of the processes a), b), c) or d) either in free form or, in the case of the presence of acidic or basic groups, converting it into physiologically tolerable salts.

Suitable protective groups E used for this are preferably the N-protective groups customary in peptide chemistry, for example protective groups of the urethane type, benzyloxycarbonyl (Z), t-butoxycarbonyl ("Boc"), 9-fluorenylmethoxycarbonyl ("Fmoc"), allyloxycarbonyl ("Aloc") or of the acid amide type, in particular formyl, acetyl or trifluoroacetyl, and of the alkyl type, for example benzyl.

Compounds of the formula III employed, in which $R^2$ is a hydrogen atom and $R^3$ is the characteristic radical of an amino acid, are preferably the characteristic radicals of the following naturally occurring α-amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid. Compounds of the formula III employed, in which $R^2$ is a hydrogen atom and $R^3$ is the characteristic radical of an amino acid, are preferably the characteristic radicals, for example, of the following non-naturally occurring amino acids: 2-aminoadipic acid, 2-aminobutyric acid, 2,4-diaminobutyric acid, 2-aminoisobutyric acid, 2,3-diaminopropionic acid, 1,2,3,4-tetrahydroisoquinoline-1-carboxylic acid, 1,2,3,4-tetrahydroisoquinoline-3-carboxylic acid, 2-amino-pimelic acid, phenylglycine, 3-(2-thienyl)alanine, 3-(3-thienyl) alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, omithine, alloisoleucine, allothreonine, 4-hydroxyproline, 3-hydroxyproline, allohydroxylysine, 3-(2-naphthyl) alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, citrulline, phosphinothricn, 4-fluorophenylalanine, 3-fluorophenylalanine, 2-fluorophenylalanine, 4-chlorophenylalanine, 4-nitrophenylalanine, 4-aminophenylalanine, cyclohexylalanine, 5-fluorotryptophan, 5-methoxytryptophan, methionine sulfone, methionine sulfoxide or $NH_2$—NH—$CONH_2$, if appropriate substituted. In the case of naturally but also of non-naturally occurring amino acids which have a functional group such as amino, hydroxyl, carboxyl, mercapto, guanidyl, imidazolyl or indolyl in the side chain $R^3$, this group can also be protected.

If there is an imidazole radical in $R^3$, the sulfonic acid derivative of the formula IV employed for the sulfonamide formation, for example, serves as a protective group for the imidazole nitrogen, which can be removed again, in particular in the presence of bases such as sodium hydroxide solution.

To prepare compounds of the formula I in which $R^2$ and $R^3$ together form a ring of the substructure II, the starting substances of the formula III utilized are, for example, 2-methylpropylphosphonic acid, piperidine-2-phosphonic acid, piperazine-2-phosphonic acid or hexahydropyridazine-3-phosphonic acid, it being possible, in particular, for the nitrogen in the 4-position of the piperazine-2-phosphonic acid to be substituted by a protective group Z, for example benzyloxycarbonyl or tert-butoxycarbonyl as described in process variant c) or by a radical $R^7$.

Starting materials used for the preparation of the sulfonic acid derivatives of the formula IV are preferably sulfonic acids or their salts of the formula X, for example

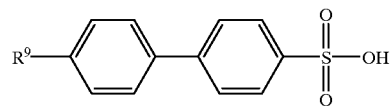

Xa

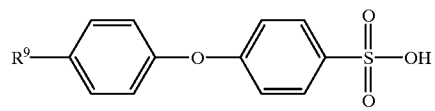

Xb

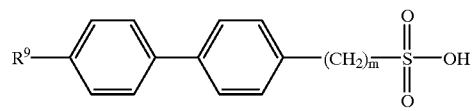

Xc

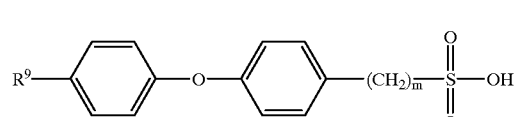

Xd

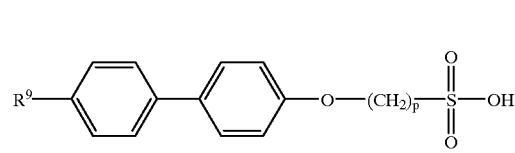

Xe

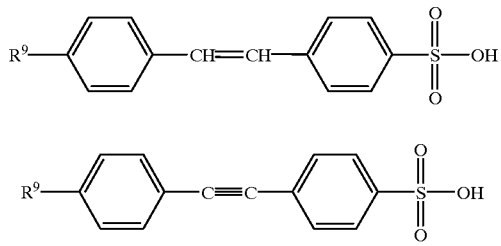

where R⁹ is a radical described under 2.1. to 2.15.

For the preparation of the arylsulfonic acids of the formulae Xa and b, the sulfonation process using concentrated sulfuric acid described in Houben-Weyl, METHODEN DER ORGANISCHEN CHEMIE [METHODS OF ORGANIC CHEMISTRY] Volume 9, pp. 450–546 is preferably used, if appropriate in the presence of a catalyst, sulfur trioxide and its addition compounds or halosulfonic acids, such as chlorosulfonic acid. Particularly in the case of the diphenyl ethers of the formula Xb, the use of concentrated sulfuric acid and acetic anhydride as a solvent (cf. C. M. Suter, 53 J. AM. CHEM. SOC. 1114 (1931)), or the reaction with excess chlorosulfonic acid (J. P. Bassin, R. Cremlyn and F. Swinbourne, 72 PHOSPHORUS, SULFUR AND SILICON 157 (1992)) has proven suitable. Sulfonic acids according to the formula Xc, Xd or Xe can be prepared in a manner known per se by reacting the corresponding arylalkyl halide with sulfites such as sodium sulfite or ammonium sulfite in aqueous or aqueous/alcoholic solution, it being possible to accelerate the reaction in the presence of tetraorganoammonium salts such as tetrabutylammonium chloride.

Sulfonic acid derivatives according to formula IV used are, in particular, the sulfonyl chlorides. For their preparation, the corresponding sulfonic acids, also in the form of their salts, such as sodium, ammonium or pyridinium salts, are reacted in a known manner with phosphorus pentachloride or thionyl chloride without or in the presence of a solvent such as phosphorus oxychloride or of an inert solvent such as methylene chloride, cyclohexane or chloroform, in general at reaction temperatures from 20° C. up to the boiling point of the reaction medium used.

The reaction of the sulfonic acid derivatives of the formula IV with the aminophosphonic acids of the formulae III, V or VII according to process variants a), b) or c) proceeds advantageously in the manner of the Schotten-Baumann reaction. Suitable bases for this are particularly alkali metal hydroxides such as sodium hydroxide, but also alkali metal acetates, hydrogencarbonates, carbonates and amines. The reaction takes place in water and/or in a water-miscible or immiscible solvent such as tetrahydrofuran ("THF"), acetone, dioxane or acetonitrile, the reaction in general being kept at from −10° C. to 50° C. If the reaction is carried out in an anhydrous medium, tetrahydrofuran or methylene chloride, acetonitrile or dioxane in the presence of a base, such as triethylamine, N-methylmorpholine, N-ethyl- or diisopropylethylamine, is especially used, possibly in the presence of N,N-dimethylaminopyridine as a catalyst.

In another variant, the aminocarboxylic acids of the formula II, IV or VII can first be converted into their silylated form with the aid of a silylating agent such as bistrimethylsilyltrifluoroacetamide ("BSTFA") and they can then be reacted with sulfonic acid derivatives to give the compounds of the formula I.

The preparation of physiologically tolerated salts from compounds of the formula I capable of salt formation, including their stereoisomeric forms, is carried out in a manner known per se. The phosphonic or phosphinic acids form stable alkali metal, alkaline earth metal or optionally substituted ammonium salts with basic reagents such as hydroxides, carbonates, hydrogencarbonates, alcoholates and also ammonia or organic bases, for example trimethyl- or triethylamine, ethanolamine or triethanolamine or alternatively basic amino acids, for example lysine, omithine or arginine. If the compounds of the formula I have basic groups, stable acid addition salts can also be prepared using strong acids. Both inorganic and organic acids such as hydrochloric, hydrobromic, sulfuric, phosphoric, methanesulfonic, benzenesulfonic, p-toluenesulfonic, 4-bromo-benzenesulfonic, cyclohexylamidosulfonic, trifluoromethylsulfonic, acetic, oxalic, tartaric, succinic or trifluoroacetic acid are suitable for this.

The invention also relates to pharmaceuticals comprising an efficacious amount of at least one compound of the formula I and/or of a physiologically tolerable salt of the compound of the formula I and/or an optionally stereoisomeric form of the compound of the formula I, together with a pharmaceutically suitable and physiologically tolerable excipient, additive and/or other active compounds and auxiliaries.

On account of the pharmacological properties, the compounds according to the invention are suitable for the prophylaxis and therapy of all those disorders in the course of which an increased activity of matrix-degrading enzymes such as metalloproteinases or aggrecanase is involved. These include degenerative joint disorders such as osteoarthroses, spondyloses, chondrolysis after joint trauma or relatively long joint immobilization after meniscus or patella injuries or torn ligaments. These furthermore also include disorders of the connective tissue such as collagenoses, periodontal disorders, wound healing disorders and chronic disorders of the locomotory apparatus such as inflammatory, immunologically or metabolically related acute and chronic arthritis, arthropathies, myalgias and disorders of the bone metabolism. The compounds of the formula I are furthermore suitable for the treatment of ulceration, atherosclerosis and stenoses. The compounds of the formula I are furthermore suitable for the treatment of inflammations, carcinomatous disorders, tumor metastasis formation, cachexia, anorexia and septic shock. In general, the pharmaceuticals according to the invention are administered orally or parenterally. Rectal or transdermal administration is also possible.

The invention also relates to a process for the production of a pharmaceutical, which comprises bringing at least one compound of the formula I into a suitable administration form using a pharmaceutically suitable and physiologically tolerable excipient and, if appropriate, further suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions and preparations with protracted release of active compound in the production of which customary auxiliaries such as excipients, disintegrants, binding agents, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, groundnut or sesame oil, polyethylene glycol and solvents such as, for example, sterile water and mono- or polyhydric alcohols such as glycerol.

The pharmaceutical preparations are preferably prepared and administered in dose units, each unit containing as active constituent a specific dose of the compound of the formula I according to the invention. In the case of solid dose units such as tablets, capsules, coated tablets or suppositories, this dose can be up to approximately 1000 mg, but preferably approximately 50 to 300 mg, and in the case of injection solutions in ampoule form up to approximately 300 mg, but preferably approximately 10 to 100 mg.

For the treatment of an adult patient weighing approximately 70 kg, depending on the efficacy of the compound according to formula I, daily doses of approximately 20 mg to 1000 mg of active compound, preferably, for example, 100 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at specific intervals.

$^1$H-NMR spectra have been recorded on a 400 MHz apparatus from Bruker or a 200 MHz apparatus from Varian, as a rule using tetramethylsilane ("TMS") as an internal standard and at room temperature ("RT"). The solvents used are indicated in each case. As a rule, final products are determined by mass-spectroscopic methods (FAB-, ESI-MS); the main peak is indicated in each case. Temperatures in degrees Celsius, RT means room temperature (22° C. to 26° C.). Abbreviations used are either explained or correspond to the customary conventions.

EXAMPLE 1

(R)-[1-(4'-Chlorobiphenyl-4-sulfonylamino)2-methylpropyl]-phosphonic Acid 250 mg (1.6 mmol) of (R)-(1-amino-2-methylpropyl) phosphonic acid were dissolved in 6 ml of a 1 M NaOH and 6 ml of tetrahydrofuran. 560 mg (1.96 mmol) of 4-chlorobiphenyl-4'-sulfonyl chloride were then added and the mixture was stirred at 22° C. overnight. The reaction mixture was concentrated, acidified with 2 M HCl and extracted with ethyl acetate. The 4-chlorobiphenyl-4'-sulfonic acid resulting as a by-product precipitated and was separated off. After drying and concentrating the ethyl acetate phase, a solid was obtained.

Yield: 136 mg (21%); molecular mass: 403.83; $^1$H-NMR: in DMSO-d6; 10.8 (s,br, 2 H); 7.91; 7.82; 7.76; 7.63 7.56 (5 d, 9 H); 3.06 (m, 1H); 1.98 (m, 1H); 0.87; 0.80 (dd, 6H); MS (ESI; M+Na$^+$): 425.9.

EXAMPLE 2

Monoethyl (R,S)-[1-(4'-chlorobiphenylsulfonylamino)-1-phenylmethyl]phosphonate 830 mg (3.85 mmol) of monoethyl (R,S)-(aminophenylmethyl)phosphonate were dissolved in 6 ml of 2 M NaOH and 10 ml of tetrahydrofuran. 1.44 g (5.01 mmol) of 4-chlorobiphenyl-4'-sulfonyl chloride were then added and the mixture was stirred at 22° C. overnight. The resultant precipitate was separated off and dispersed in hot water/ethyl acetate. After acidifying with HCl to pH 1 to 2, the ethyl acetate phase was separated off and concentrated. A solid remained.

Yield: 610 mg (34%); molecular mass: 465; $^1$H-NMR: in DMSO-d6; 8.66 (s, br, 1 H); 7.57 (m, 9 H); 7.16 (m, 2 H); 7.01 (m, 3 H); 4.58 (dd, 1 H) 3.85 (m, 2H); 1.11 (m, 3H); MS (FAB; M$^+$, M+Na$^+$): 466.0; 488.0.

EXAMPLE 3

(R,S)-[(4'-Chlorobiphenyl-4-sulfonylamino)phenylmethyl]-phosphonic Acid 320 mg (0.69 mmol) of the monoethyl ester from Example 2 were dissolved in 6 ml of dichloromethane and treated at 0° C. with 0.36 ml (2.75 mmol) of trimethylsilyl bromide. After 4 h at RT, the reaction mixture was concentrated to dryness on a rotary evaporator and the residue which remained was taken up in water. Solids were removed and the aqueous phase was freeze-dried.

Yield: 257 mg (80%); molecular mass: 436.8 g/mol; $^1$H-NMR: DMSO-d$_6$; 7.6 (m, 8 H); 7.2 (m, 2 H); 7.0 (m, 3 H); 4.2 (m, 1 H); MS (ESI$^-$): 436.0.

EXAMPLE 4

(R,S)-[1-(4'-Chlorobiphenyl-4-sulfonylamino)-2-(1H-indol-3-yl)-ethyl]phosphonic Acid 150 mg (0.274 mmol) of the corresponding diethyl ester were dissolved in 4 ml of dichloromethane and treated at room temperature with 0.11 ml (0.82 mmol) of trimethylsilyl bromide. After 3 h, the reaction mixture was concentrated to dryness on a rotary evaporator, the residue which remained was treated with diisopropyl ether and the solid was removed by filtration.

Yield: 42 mg (33%); molecular mass: 490.92; $^1$H-NMR: DMSO-d$_6$; 10.4 (s, 2 H); 7.9; 7.68; 7.55 (3 d, 5 H); 7.3; 6.9 (2 m, 8 H); 3.7 (m, 1 H); 3.2–2.6 (2 m, 4H); MS (ESI$^+$): 491.0.

EXAMPLE 5

(R,S)-[1-(4'-Chlorobiphenyl-4-sulfonylamino)ethyl]phosphonic Acid 733 mg (2.8 mmol) of N,O-bistrimethylsilyltrifluoroacetamide were added under nitrogen to 178 mg (1.4 mmol) of (R,S)-1-aminoethyl phosphonic acid in 30 ml of acetonitrile and the mixture was heated under reflux for 2 h. After cooling to 15° C., 490 mg (1.7 mmol) of 4'-chlorobiphenyl-4-sulfonyl chloride in 15 ml of acetonitrile were added. The mixture was stirred at RT for 3 h, concentrated, treated with methanol and concentrated again.

The residue was chromatographed on silica gel using methylene chloride/methanol 75:25 and 1% acetic acid.

Yield: 60 mg (11%), molecular mass: 375.77; $^1$H-NMR: DMSO-d$_6$; 1.0–1.2 (m, 3H), 3.35–3.55 (m, 1 H), 7.5 (d, 2H), 7.68 (d, 2H), 7.8 (d, 2H), 8.0 (d, 2H); MS (ESI$^-$): 374.1.

EXAMPLE 6

(R,S)-[1-(4'-chlorobiphenyl-4-sulfonylamino)-3-methylbutyl]-phosphonic Acid 516 mg (2 mmol) of N,O-bistrimethylsilyltrifluoroacetamide were added under nitrogen to 222 mg (1 mmol) of (R,S)-1-amino-3-methylbutylphosphonic acid hydrochloride in 30 ml of acetonitrile and the mixture was heated under reflux for 2 h. After cooling to 15° C., 345 mg (1.2 mmol) of 4'-chlorobiphenyl-4-sulfonyl chloride in 15 ml of acetonitrile were added. The mixture was stirred for 3.5 h at RT, concentrated, treated with methanol and concentrated. The residue was chromatographed on RP18 using acetonitrile/water (contains 0.1% trifluoroacetic acid), gradient 10% to 100% acetonitrile.

Yield: 75 mg (18%), molecular mass: 417.85; MS (ESI$^-$): 416.1.

The compounds defined in Table 1 below were prepared analogously to Examples 1 to 6.

TABLE 1

| Ex. | Structure | $^1$H—NMR | M$^+$ or M$^-$ |
|---|---|---|---|
| 1 | 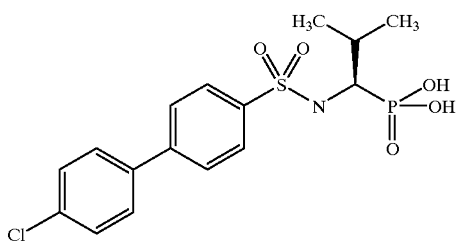 | see text | see text |
| 2 | 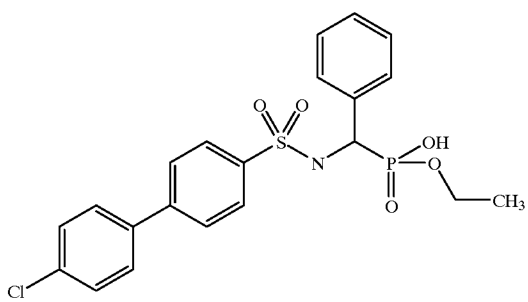 | see text | see text |
| 3 | 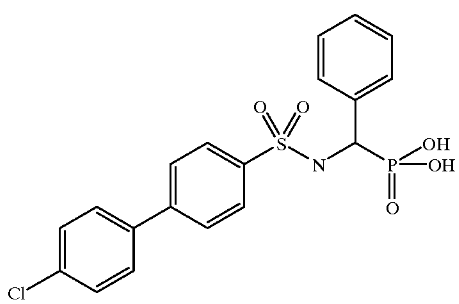 | see text | see text |
| 4 | 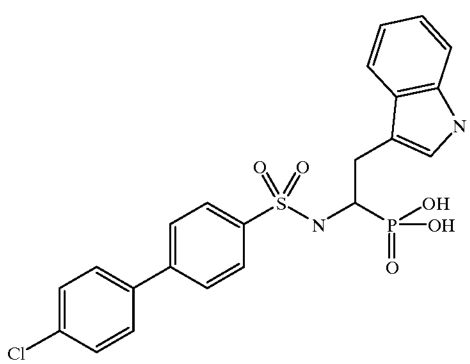 | see text | see text |
| 5 | 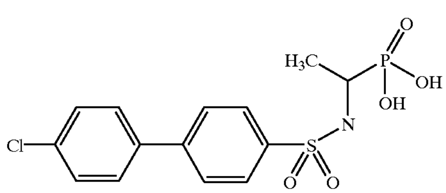 | see text | see text |

TABLE 1-continued

| Ex. | Structure | ¹H—NMR | M⁺ or M⁻ |
|---|---|---|---|
| 6 | 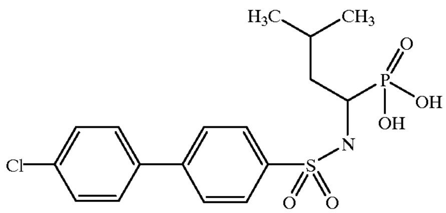 | see text | see text |
| 7 | Chiral | 09–1.15(m, 6H), 3.65–4.1 (m, 2H), 7.5–8.0(m, 10H) | 447.1 (+) |
| 8 | 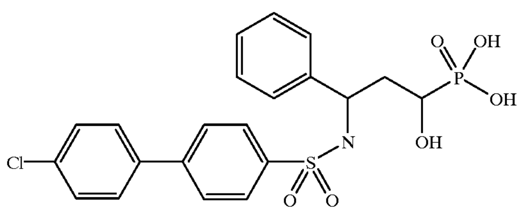 | 1.85-2.1(m, 2H), 2.8–3.0 (m, 1H), 4.45–4.75(m, 1H), 6.98–7.18(m, 5H), 7.5–7.75 (m, 8H), 8.35(m, 1H) | 480.1 (−) |
| 9 | 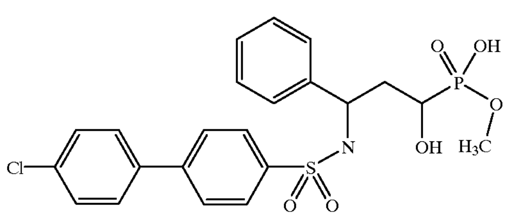 | 1.8–2.0(m, 2H), 3.1–3.3 (m, 1H), 3.4–3.7(2xd, 3H), 4.55–4.75(m, 1H), 7.0–7.15 (m, 5H), 7.4–7.65(m, 8H) | 494.1 (−) |
| 10 | 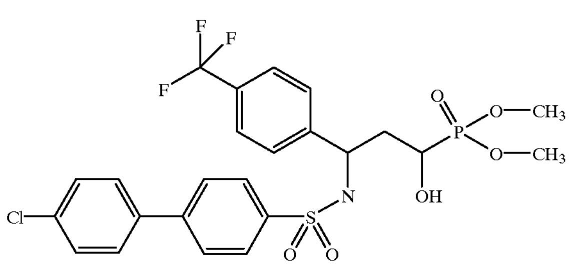 | 1.8–2.1(m, 2H), 3.05–3.25 (m, 1H), 3.5–3.7(6H), 4.45–4.65(m, 1H), 5.5–6.1 (b, 1H), 7.3(d, 2H), 7.35–7.7(m, 10H), 8.4–8.7 (b, 1H) | 578.1 (+) |

TABLE 1-continued

| Ex. | Structure | $^1$H—NMR | M$^+$ or M$^-$ |
|---|---|---|---|
| 11 | 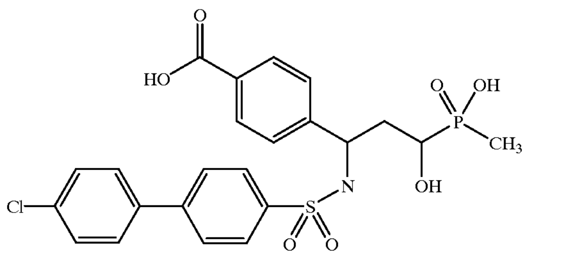 | 1.07–1.32(3H), 1.8–2.15 (m, 2H), 2.75–2.95(m, 1H), 4.5–4.78(m, 1H), 5.25–5.6 (b, 1H), 7.2(m, 2H), 7.42–7.72(m, 10H), 8.5(t, 1H) | 522.1 (−) |
| 12 | 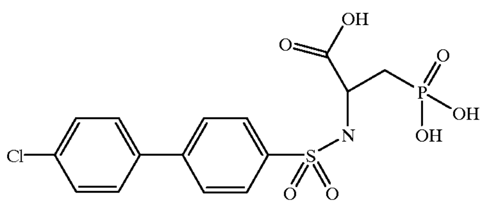 | 1.55–1.75(m, 1H), 1.8–2.05 (m, 1H), 3.8–4.0(m, 1H), 7.55(d, 2H), 7.75(d, 2H), 7.78–7.85(m, 4H), 8.0–8.2 (b, 1H) | 418.1 (−) |
| 13 | 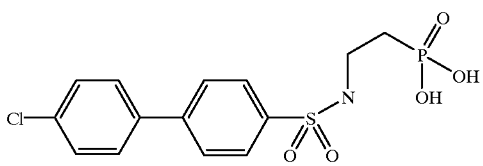 | 1.6–1.8(m, 2H), 2.85–3.05 (m, 2H), 7.6(d, 2H), 7.65–8.0(m, 7H) | 374.1 (−) |
| 14 | 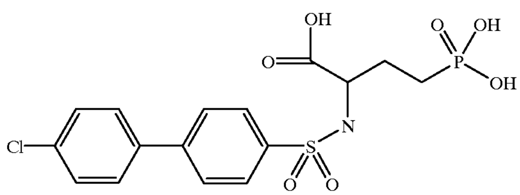 | 1.4–2.1(m, 4H), 3.95 (t, 1H), 7.5(d, 2H), 7.69 (d, 2H), 7.83(d, 2H), 7.92 (d, 2H) | 433.9 (+) |
| 15 | 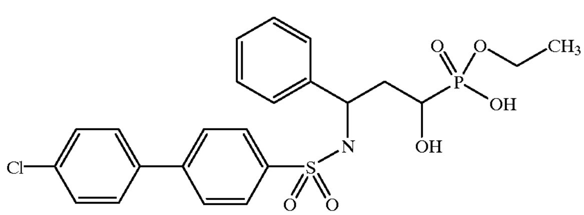 | 0.7–1.5(m, 3H), 1.8–2.05 (m, 2H), 3.7–3.95(m, 2H), 4.4–4.6(m, 1H), 6.9–7.2 (m, 4H), 7.45–7.78(m, 9H), 8.4(d, 1H) | 510.0 (+) |
| 16 | 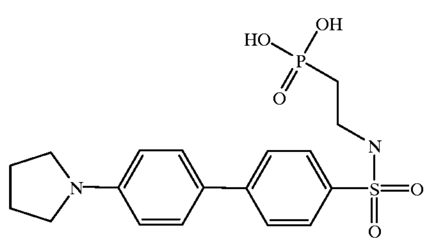 | 1.55–2.1(m, 6H), 2.8–3.05 (m, 2H), 3.2–3.4(m, 4H), 6.65(d, 2H), 7.5–7.9 (m, 6H) | 411.1 (+) |
| 17 | 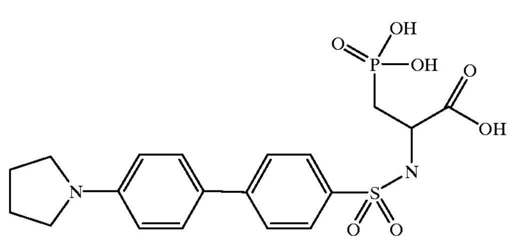 | 1.6–2.2(m, 6H), 3.15–3.4 (m, 4H), 3.8–4.1(m, 1H), 6.55(d, 2H), 7.62(d, 2H), 7.75(s, 4H), 7.9–8.1(b, 1H) | 455.1 (+) |

TABLE 1-continued

| Ex. | Structure | ¹H—NMR | M⁺ or M⁻ |
|---|---|---|---|
| 18 | (Chiral) 4-chlorobiphenyl-sulfonamide with isobutyl-phosphonic acid | 0.8(d, 3H), 0.9(d, 3H), 1.85–2.1(m, 1H), 3.3–3.5 (m, 1H), 7.55(d, 2H), 7.6–7.7(m, 1H), 7.8(d, 2H), 7.82(d, 2H), 7.9(d, 2H) | 404.1 (+) |
| 19 | (Chiral) 4-pyrrolidinyl-biphenyl-sulfonamide with isobutyl-phosphonic acid · TFA | 0.8(d, 3H), 0.9(d, 3H), 1.85–2.1(m, 5H), 3.2–3.35 (m, 4H), 3.36–3.5(m, 1H), 6.62(d, 2H), 7.5(dd, 1H), 7.6(d, 2H), 7.7(d, 2H), 7.82(d, 2H) | 437.2 (−) |
| 20 | 4-chlorobiphenyl-ethyl-sulfonamide with ethyl-phosphonic acid | 1.28(d, 1.5H), 1.35 (d, 1.5H), 2.9–3.6(m, 6H), 7.25–7.8(m, 8H) | 402.1 (−) |
| 21 | bis(4-chlorobiphenyl-sulfonyl) glutamic acid phosphonate | — | 710.9 (−) |
| 22 | 4-pyrrolidinyl-biphenyl-sulfonamide with ethyl-phosphonic acid · TFA | 0.88(d, 1.5H), 0.95 (d, 1.5H), 1.9–2.1(m, 4H), 3.3–3.4(m, 5H), 6.63 (d, 2H), 7.55–7.9(m, 7H) | 409.2 (−) |
| 23 | (Chiral) biphenyl-carboxamide with isopropyl-phosphonic acid | 0.95, 1.05(d, 6H), 2.07–2.32(m, 1H), 4.07–4.3 (m, 1H), 7.35–7.59(m, 3H), 7.67–7.82(m, 4H), 8.0 (d, 2H) | 332.1 (−) |

TABLE 1-continued

| Ex. | Structure | $^1$H—NMR | M$^+$ or M$^-$ |
|---|---|---|---|
| 24 | (Chiral structure) | — | 364.2 (−) |
| 25 | (structure) | 0.98(d, 3H), 2.0–2.15 (m, 1H), 2.9–3.05(m, 1H), 3.1–3.2(m, 1H), 3.25–3.5 (m, 3H), 7.2(dd, 1H), 7.4 (d, 2H), 7.5(d, 2H), 7.6 (d, 2H), 7.7(d, 2H) | 432.1 (+) |

Pharmacological Examples

Preparation and determination of the enzymatic activity of the catalytic domain of human stromelysin and of neutrophil collagenase.

The two enzymes—stromelysin ("MMP-3") and neutrophil collagenase ("MMP-8")—were prepared according to Ye et al., 31 BIOCHEMISTRY 11231 (1992). For the measurement of the enzyme activity or of the enzyme inhibitor action, 70 μl of buffer solution and 10 μl of enzyme solution are incubated for 15 minutes with 10 μl of a 10% strength (v/v) aqueous dimethyl sulfoxide solution which optionally contains the enzyme inhibitor. After addition of 10 μl of a 10% strength (v/v) aqueous dimethyl sulfoxide solution which contains 1 mmol/l of the substrate, the enzyme reaction is monitored by fluorescence spectroscopy (328 nm (ex)/1393 nm(em)).

The enzyme activity is shown as extinction increase/minute. The IC$_{50}$ values listed in Table 2 are determined as those inhibitor concentrations which in each case lead to a 50% inhibition of the enzyme.

The buffer solution contains 0.05% Brij (Sigma, Deisenhofen, Germany) and 0.1 mol/l of tris/HCl, 0.1 mol/l of NaCl, 0.01 mol/l of CaCl$_2$ and 0.1 mol/l of piperazine-N,N'-bis[2-ethanesulfonic acid] (pH=6.5).

The enzyme solution contains 5 μg/ml of one of the enzyme domains prepared according to Ye et al. The substrate solution contains 1 mmol/l of the fluorogenic substrate 7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany).

TABLE 2

| Example No. | Stromelysin IC$_{50}$ (M) | Neutrophil collagenase IC$_{50}$ (M) |
|---|---|---|
| 1 | 6 × 10$^{-9}$ | 1 × 10$^{-9}$ |
| 2 | 5 × 10$^{-6}$ | 2 × 10$^{-7}$ |
| 3 | 1 × 10$^{-7}$ | 7 × 10$^{-9}$ |
| 4 | 5 × 10$^{-7}$ | 6 × 10$^{-8}$ |
| 5 | 1 × 10$^{-7}$ | 5 × 10$^{-9}$ |
| 6 | 3 × 10$^{-8}$ | 3 × 10$^{-9}$ |
| 18 | 1 × 10$^{-5}$ | 1 × 10$^{-6}$ |
| 19 | 5 × 10$^{-9}$ | 2 × 10$^{-9}$ |
| 20 | 8 × 10$^{-9}$ | 2 × 10$^{-9}$ |
| 22 | 2 × 10$^{-8}$ | 2 × 10$^{-8}$ |
| 24 | 4 × 10$^{-7}$ | 3 × 10$^{-8}$ |
| 25 | 3 × 10$^{-9}$ | 2 × 10$^{-9}$ |

Preparation and determination of the enzymatic activity of the catalytic domain of aggrecanase using rat chondrosarcoma cells:

For the generation of the as yet not identified "aggrecanase" activity, rat chondrosarcoma cells (RCS) were used. Lark et al.; 270 J. BIOL. CHEM. 2550 (1995). These cells were inoculated into 96well cell culture plates precoated with poly-L-lysine (80,000 cells/well). After stimulation of the RCS cells with retinoic acid (0.67 μM) and an incubation time of 47 hours (h) at 37° C. and 5% CO$_2$, these cells generate the "aggrecanase" activity. The test substance compound 1 was then preincubated for 1 h in the "aggrecanase"-containing cell culture supernatant before 5 μg of eucaryotic rAgg1$_{mut}$ (Büttner et al., 333 BIOCHEM. J. 159 (1998); Hughes et al., 272 J. BIOL. CHEM. 20269 (1997)) were added for the detection of the "aggrecanase" cleavage activity in the cell culture supernatant of the RCS cells. After an incubation time of 4 h, the cell culture supernatant was removed and the cleavage products of the rAgg1$_{mut}$ fusion proteins generated by the "aggrecanase" activity were detected by means of SDS-polyacrylamide gel electrophoresis and Western Blot analyses with the monoclonal antibody BC-3. Hughes et al., 305 BIOCHEM. J. 799 (1995). The action of the compound 1 was seen in the lowering of the BC-3 reactive cleavage products. The less cleaved rAgg1$_{mut}$ was detected, the more efficacious was the tested compound of the formula I.

The IC$_{50}$ values listed in Table 3 are determined as those inhibitor concentrations which in each case led to a 50% inhibition of the enzyme aggrecanase.

TABLE 3

| Example No. | Aggrecanase IC$_{50}$ | |
| --- | --- | --- |
| 1 | 0.6 | $10^{-6}$ M |
| 2 | 79 | $10^{-6}$ M |
| 3 | 22 | $10^{-6}$ M |
| 4 | 12 | $10^{-6}$ M |
| 5 | 25 | $10^{-6}$ M |
| 6 | 2.4 | $10^{-6}$ M |
| 7 | 29 | $10^{-6}$ M |
| 8 | 15 | $10^{-6}$ M |
| 10 | 2.1 | $10^{-6}$ M |
| 12 | 50 | $10^{-6}$ M |
| 13 | 50 | $10^{-6}$ M |
| 14 | 55 | $10^{-6}$ M |
| 15 | 67 | $10^{-6}$ M |
| 16 | 28 | $10^{-6}$ M |
| 17 | 69 | $10^{-6}$ M |
| 18 | 60 | $10^{-6}$ M |
| 20 | 4.7 | $10^{-6}$ M |
| 21 | 0.52 | $10^{-6}$ M |
| 22 | 8.3 | $10^{-6}$ M |

The invention may be embodied in other specific forms and those skilled in the art will recognize that various changes and modifications can be made without departing from the spirit or essential characteristics thereof. The present embodiment is, therefore, considered in all respects as illustrative and not restrictive. Embodiments are measured by the scope of the appended claims rather than by the foregoing description, and all changes which come within the meaning and range of equivalency of the claims are therefore intended to be embraced therein.

We claim:

1. A compound of formula I

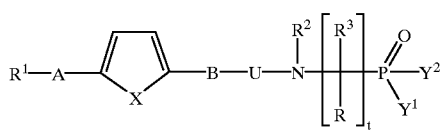

(I)

a stereoisomeric form thereof, or a physiologically tolerable salt thereof, where (A.) $R^1$ is
1. phenyl;
2. phenyl, which is mono- or disubstituted by
   2.1 $(C_1-C_6)$-alkyl,
   2.2 hydroxyl,
   2.3. $(C_1-C_6)$-alkyl-C(O)—O—,
   2.4. $(C_1-C_6)$-alkyl-O—,
   2.5. $(C_1-C_6)$-alkyl-O-$(C_1-C_4)$-alkyl-O—,
   2.6. halogen,
   2.7. —CF$_3$,
   2.8. —CN,
   2.9. —NO$_2$,
   2.10. HO—C(O)—,
   2.11. $(C_1-C_6)$-alkyl-O—C(O)—,
   2.12. methylenedioxo,
   2.13. $R^4$—($R^5$)N—C(O)—,
   2.14. $R^4$—($R^5$)N—, or
   2.15 a residue described under A.3.1 to A.3.16;
3. a residue described under A.3.1 to A.3.16, which is unsubstituted or substituted by one or more radicals described under A.2.1 to A.2.15, 3.1. pyrrole,
3.2. pyrazole,
3.3. imidazole,
3.4. triazole,
3.5. thiophene,
3.6. thiazole,
3.7. oxazole,
3.8. isoxazole,
3.9. pyridine,
3.10. pyrimidine,
3.11. pyrrolidine,
3.12. indole,
3.13. benzothiophene,
3.14. benzimidazole,
3.15. benzoxazole, or
3.16. benzothiazole; or 4. —O-$(C_1-C_6)$-alkyl;

(B1.) $R^2$ is
1. a hydrogen atom;
2. $(C_1-C_6)$-alkyl-;
3. Phenyl-$(CH_2)_n$—, in which phenyl is unsubstituted or mono- or disubstituted with radicals described under A.2.1 to A.2.15, or is substituted by —NH—C(O)-$(C_1-C_3)$-alkyl, and n is the integer zero, 1, or 2; or
4. picolyl;

(B2.) $R^4$ and $R^5$ independently of one another are identical or different and are
1. a hydrogen atom;
2. $(C_1-C_6)$-alkyl-;
3. HO—C(O)-$(C_1-C_6)$-alkyl-;
4. phenyl-$(CH_2)_n$—, in which phenyl is unsubstituted or mono- or disubstituted with radicals described under A.2.1 to A.2.15, or is substituted by —NH—C(O)-$(C_1-C_3)$-alkyl, and n is the integer zero, 1, or 2;
5. picolyl; or
6. $R^4$ and $R^5$, together with the nitrogen to which they are bonded, form a 4- to 7-membered ring, and the ring is unsubstituted, or a carbon atom in the ring is replaced by —O—, —S—, or —NH—, or two adjacent carbon atoms of the 4- to 7-membered ring are part of a benzyl radical;

(C.) R and $R^3$ are identical or different and are
1. a hydrogen atom;
2. $(C_1-C_{10})$-alkyl-, in which alkyl is unsubstituted or monosubstituted by —OH;
3. $(C_2-C_{10})$-alkenyl-, in which alkenyl is linear or branched;
4. $R^2$—O-$(C_1-C_6)$-alkyl-;
5. $R^2$—S(O)$_n$-$(C_1-C_6)$-alkyl-, where n is the integer zero, 1, or 2;
6. $R^2$—S(O)(=NH)-$(C_1-C_6)$-alkyl-;
7. a radical of formula IIo

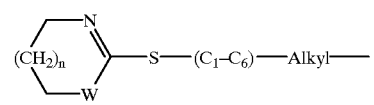

(IIo)

in which n is the integer zero, 1, or 2, and W is a nitrogen, oxygen, or sulfur atom;

8. phenyl-$(CH_2)_m$—, in which m is the integer zero, 1, 2, 3, 4, 5, or 6, wherein the —$(CH_2)_m$— chain is unsubstituted or monosubstituted by —OH, and wherein phenyl is unsubstituted or mono- or disubstituted by
8.1 radicals described under A.2.1 to A.2.15,
8.2 —O—$(CH_2)_m$-phenyl, in which phenyl is unsubstituted or mono- or disubstituted with radicals described under A.2.1 to A.2.15, and m is the integer zero, 1, 2, 3, 4, 5, or 6,
8.3 —C(O)—$(CH_2)_m$-phenyl, in which phenyl is defined under C.8.2;
9. residue-$(CH_2)_m$—, in which residue is defined under A.3.1 to A.3.16, m is defined under C.8, the —$(CH_2)_m$— chain is unsubstituted or monosubstituted by —OH, and residue is unsubstituted or mono- or disubstituted by
9.1 radicals described under A.2.1 to A.2.15,
9.2 —CH(O),
9.3 —$SO_2$-phenyl, in which phenyl is unsubstituted or substituted as defined under C.8.2 or C.8.3,
9.4 —O—$(CH_2)_m$-phenyl;
10. —$(CH_2)_m$—P(O)(OH)-$(C_1-C_3)$-alkyl, in which m is defined under C.8;
11. a characteristic radical of an amino acid;
12. $R^6$—C(O)-$(C_0-C_6)$-alkyl- in which $R^6$ is
12.1. a hydrogen atom,
12.2. $(C_1-C_6)$-alkyl-,
12.3. phenyl, which is unsubstituted or substituted with one or more radicals described under A.2.1 to A.2.15,
12.4. residue, which is defined under A.3.1 to A.3.16, and is unsubstituted or substituted with one or more radicals described under A.2.1 to A.2.15, or is substituted by -$(C_1-C_4)$-alkyl-COOH,
12.5. —OH,
12.6. —$OR^2$, in which $R^2$ has the meaning described under B1.1 to B1.4,
12.7. —$NR^4$—$(R^5)$, in which $R^4$ and $R^5$ are defined under B2.1 to B2.6,
12.8. residue-$(CH_2)_m$—NH—, in which residue is defined under A.3.1 to A.3.16, and is unsubstituted or substituted with one or more radicals described under A.2.1 to A.2.15, and m is defined under C.8,
12.9. $R^4$—$(R^5)$N—NH—, in which $R^4$ and $R^5$ are defined under B2.1 to B2.6,
12.10. HO—C(O)—CH($R^3$)—NH—, in which $R^3$ is defined under C.1 to C.11;
13. —$(CH_2)_p$—N($R^9$)($R^{10}$), in which p is an integer zero, 1, 2, 3, or 4, in which $R^9$ and $R^{10}$ are identical or different and are
13.1. a hydrogen atom,
13.2. phenyl-$(CH_2)_m$—, in which phenyl is unsubstituted or mono- or disubstituted with radicals described under A.2.1 to A.2.15, and m is the integer zero, 1, 2, or 3,
13.3. $R^x$—C(O)—, in which $R^x$ is
3.1 $(C_1-C_6)$-alkyl-,
3.2 $(C_2-C_6)$-alkenyl-,
3.3 phenyl-$(CH_2)_m$—, in which phenyl is unsubstituted or mono- or disubstituted with radicals described under A.2.1 to A.2.1 115, and m is the integer zero, 1, 2, or 3, or
3.4 residue-$(CH_2)_m$—, in which residue is defined under A.3.1 to A.3.16,
13.4. $R^x$—O—C(O)—, in which $R^x$ is defined under C.13.3,
13.5. $R^x$—CH($NH_2$)—C(O)—, in which $R^x$ is defined under C.13.3,
13.6. $R^8$—N($R^7$)—C(O)—, in which $R^8$ is
6.1 a hydrogen atom
6.2 $(C_1-C_6)$-alkyl-,
6.3 phenyl-$(CH_2)_m$—, in which phenyl is unsubstituted or mono- or disubstituted with radicals described under A.2.1 to A.2.15, and m is the integer zero, 1, 2, or 3, or
6.4 residue-$(CH_2)_m$—, in which residue is defined under A.3.1 to A.3.16, and is unsubstituted or substituted with one or more radicals described under A.2.1 to A.2.15, m is the integer zero, 1, 2, or 3, and in which $R^7$ is a hydrogen atom or $(C_1-C_6)$-alkyl-, or in which $R^7$ and $R^8$, together with the nitrogen atom to which they are bonded, form a 4- to 7-membered ring, and the ring is unsubstituted or a carbon atom in the ring is replaced by —O—, —S—, or —NH—,
13.7. $R^x$—$SO_2$—, in which $R^x$ is defined under C.13.3,
13.8. $R^x$—NH—C(=$NR^7$)—, in which $R^x$ is defined under C.13.3 and $R^7$ is defined under C.13.6.4, or $R^x$ and $R^7$ are
8.1 $(C_1-C_6)$-alkyl-C(O)—,
8.2 —$NO_2$ or
8.3 —$SO_2$—$(CH_2)_q$-phenyl, in which phenyl is unsubstituted or mono- or disubstituted with radicals described under A.2.1 to A.2.15, and q is the integer zero, 1, 2, or 3,
13.9. —$SO_2$—$(CH_2)_q$-phenyl-phenyl, in which each phenyl independently is unsubstituted or mono- or disubstituted with radicals described under A.2.1 to A.2.15, and q is the integer zero, 1, 2, or 3, or
13.10. a radical of formula IIp

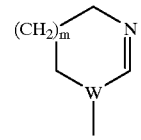

(IIp)

in which m is the integer zero, 1, 2, or 3, and W is a nitrogen atom or sulfur atom, or
$R^9$ and $R^{10}$, together with the nitrogen atom to which they are bonded, form a ring chosen from radicals of the subformulae IIa to IIn,

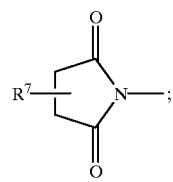

(IIa)

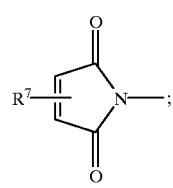

(IIb)

-continued (IIc) 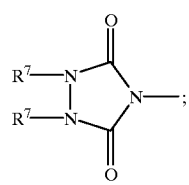

(IId) 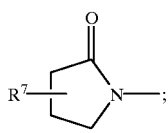

(IIe) 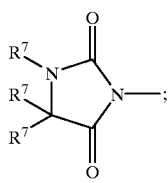

(IIf) 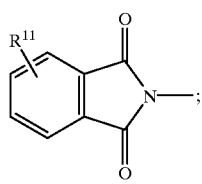

(IIg) 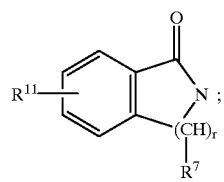

(IIh) 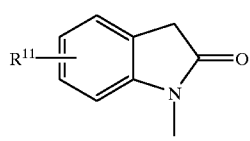

(IIi) 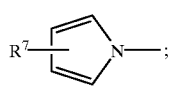

(IIj) 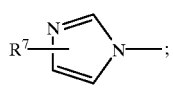

(IIk) 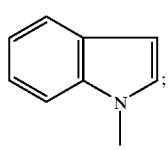

(IIl) 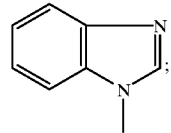

(IIm) 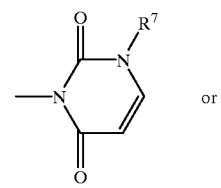

or (IIn) 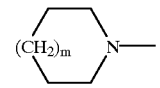

where r is the integer 1 or 2, $R^{11}$ is a radical described under A.2.1 to A.2.15, $R^7$ is defined under C.13.6.4, and m is defined under C.13.2, and a carbon atom in the ring is replaced by zero or one herospecies chosen from oxygen, sulfur, or nitrogen atom which is unsubstituted or monosubstituted with $R^2$;

14. —OH;
15. =O;
16. $(C_1-C_6)$-alkyl-; or in the compound of formula I, a —C(R)($R^3$)— radical is optionally replaced by —NH— or —$NR^2$— in which $R^2$ is defined under B1.1 to B1.4;

(D.) t is an integer 1, 2, 3, or 4;

(E.) alternatively, $R^2$ and $R^3$ together form a ring with an exocyclic phosphinic or phosphonic acid radical of the subformula II (II) 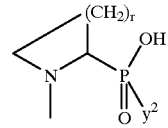

in which r is the integer zero, 1, 2, or 3, and one carbon atom in the ring of the radical of subformula II is replaced by zero or one herospecies chosen from —O—, —S—, or —($R^7$)N—, in which $R^7$ is 1. a hydrogen atom;
2. $(C_1-C_6)$-alkyl;
3. phenyl, in which phenyl is unsubstituted or substituted with one or more radicals described under A.2.1 to A.2.15;
4. benzyl, in which benzyl is unsubstituted or substituted with one or more radicals described under A.2.1 to A.2.15; or
5. $R^2$N—C(=NH)— where $R^2$ has the meaning described under B1.1 to B1.4, and the carbon atoms in the ring of the subformula II are unsubstituted or mono- or polysubstituted by $(C_1-C_6)$-alkyl-, phenyl-, phenyl-$(CH_2)_m$— or HO—, or combinations thereof;

(F.) U is —SO$_2$—;
(G.) Y$^1$ is —OH and Y$^2$ is
  a) a hydrogen atom;
  b) —OH;
  c) —(CH$_2$)$_u$-phenyl, in which u is zero or 1;
  d) —O-(C$_1$–C$_4$)-alkyl, in which alkyl is linear or branched; or
  e) —O-(CH$_2$)$_s$-phenyl, in which s is zero or 1;
(H.) A is
  a) a covalent bond;
  b) —O—;
  c) —CH═CH—; or
  d) —C≡C—;
(I.) B is
  a) —(CH$_2$)$_m$—, in which m is defined under C.13.2;
  b) —O—(CH$_2$)$_p$, in which p is an integer from 1 to 5; or
  c) —CH═CH—; and
(J.) X is —CH═CH—.

2. The compound of formula I as claimed in claim 1, wherein
R$^1$ is
  1. phenyl;
  2. phenyl which is monosubstituted by
    2.1. (C$_1$–C$_6$)-alkyl-,
    2.2. —OH,
    2.3. —C(O)—OH,
    2.4. —O-(C$_1$–C$_6$)-alkyl,
    2.5. pyrrolidone,
    2.6. halogen, or
    2.7. —CF$_3$; or
  3. —O-(C$_1$–C$_6$)-alkyl;
R$^2$, R$^4$ and R$^5$ are identical or different and are a hydrogen atom or (C$_1$–C$_6$)-alkyl-;
R is a hydrogen atom;
R$^3$ is
  1. (C$_1$–C$_6$)-alkyl-, in which alkyl is unsubstituted or monosubstituted by —OH,
  2. R$^2$—S(O)$_n$-(C$_1$–C$_6$)-alkyl-, in which R$^2$ is (C$_1$–C$_6$)-alkyl- or phenyl-(CH$_2$)$_n$—, and n is the integer zero or 1;
  3. —(CH$_2$)$_m$-phenyl, in which phenyl is unsubstituted or mono- or disubstituted with radicals described under A.2.1 to A.2.15 in claim 1, the —(CH$_2$)$_m$— chain is unsubstituted or monosubstituted by —OH, and m is the integer 1, 2, 3, 4, or 5;
  4. —(CH$_2$)$_m$-residue, in which residue has the meaning mentioned under A.3.3, A.3.5, A.3.6, A.3.9, or A.3.11 in claim 1, and is unsubstituted or substituted with one or more radicals described under A.2.1 to A.2.15 in claim 1, the —(CH$_2$)$_m$— chain is unsubstituted or monosubstituted by —OH, and m is the integer 1, 2, 3, or 4;
  5. a characteristic radical of an amino acid;
  6. —(CH$_2$)$_p$—N(R$^9$)(R$^{10}$), in which p is the integer zero, 1, or 2 in which R$^9$ and R$^{10}$ are identical or different and are a hydrogen atom or —SO$_2$—(CH$_2$)$_q$-phenyl-phenyl, in which each phenyl independently is unsubstituted or mono- or disubstituted with radicals described under A.2.1 to A.2.15 in claim 1, and q is the integer zero, 1, 2, or 3; or
  7. R$^6$—C(O)—, in which R$^6$ is
    7.1. —OH,
    7.2. R$^2$O—, in which R$^2$ is defined under B1.1 to B1.4 in claim 1, or
    7.3. R$^4$—(R$^5$)N—, in which R$^4$ and R$^5$ are defined under B2.1 to B2.6 in claim 1;
  8. a hydrogen atom;
  9. —OH;
  10. ═O; or
  11. (C$_1$–C$_6$)-alkyl-; or
in the compound of formula I, a —C(R)(R$^3$)-radical is optionally replaced by —NH— or —NR$^2$—, in which R$^2$ is defined under B1.1 to B1.4 in claim 1; and
t is an integer 1, 2, 3, or 4;
U is —SO$_2$—;
Y$^1$ is —OH;
Y$^2$ is a) —O-(C$_1$–C$_4$)-alkyl, in which alkyl is linear or branched, or
  b) —OH;
A is a covalent bond or —O—;
B is a covalent bond or -(C$_1$–C$_4$)-alkyl; and
X is —CH═CH—.

3. A compound of formula I as claimed in claim 1, wherein
R$^1$ is phenyl which is monosubstituted by halogen;
R$^2$ is a hydrogen atom;
R is a hydrogen atom;
R$^3$ is
  1. (C$_1$–C$_4$)-alkyl-;
  2. -phenyl, in which phenyl is unsubstituted or mono- or disubstituted by —CF$_3$ or —COOH;
  3. a hydrogen atom;
  4. —OH; or
  5. —NH—SO$_2$-phenyl-phenyl, in which each phenyl independently is unsubstituted or substituted by one ore more identical or different halogen atoms;
t is an integer 1, 2, 3, or 4;
U is —SO$_2$—;
Y$^2$ is —OH or —O—CH$_3$;
A is a covalent bond;
B is a covalent bond or —(CH$_2$)$_o$—, in which o is 1, 2, or 3; and
X is —CH═CH—.

4. A compound chosen from (R )-[1-(4'-chlorobiphenyl-4-sulfonylamino)-2-methylpropyl]phosphonic acid, dimethyl-[3-(4'-chlorobiphenyl-4-sulfonylamino)-1-hydroxy-3-(4-trifluoromethylphenyl)propyl]phosphonate, [1-(4'-chlorobiphenyl-4-sulfonylamino)-3-methylbutyl]-phosphonic acid, monoethyl-(R,S)-[1-(4'-chlorobiphenyl-4-sulfonylamino)-1-phenylmethyl]phosphonate, a stereoisomeric form of said compound, and a physiologically tolerable salt of any of the foregoing.

5. The compound, as claimed in claim 4, chosen from (R)-[1-(4'-chlorobiphenyl-4-sulfonylamino)-2-methylpropyl]phosphonic acid, [1-(4'-chlorobiphenyl-4-sulfonylamino)-3-methylbutyl]-phosphonic acid, monoethyl-(R,S)-[-1-(4'-chlorobiphenyl-4-sulfonylamino)-1-phenylmethyl]phosphonate, a stereoisomeric form of said compound, and a physiologically tolerable salt of any of the foregoing.

6. A process for preparing a compound of formula I as described in claim 1, comprising the step of:
reacting an aminophosphinic or -phosphonic acid of formula III,

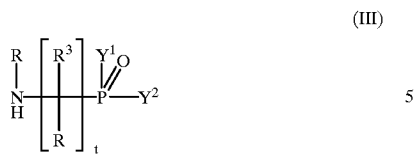

(III)

in which $R^2$, $Y^1$, $Y^2$, t, R, and $R^3$ are as defined in formula I, with a sulfonic acid or carbonyl derivative of formula IV

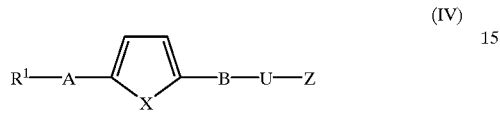

(IV)

in which $R^1$, A, X, U, and B are as defined in formula I, and Z is a halogen atom, imidazolyl, or —$OR^8$, in which $R^8$ is a hydrogen atom, $(C_1$–$C_6)$-alkyl, phenyl or benzyl, wherein said alkyl, phenyl, or benzyl is independently unsubstituted or substituted, in the presence of a base to give a compound of formula I.

7. The process as claimed in claim 6, wherein the reacting step is performed in the presence of a dehydrating agent.

8. The process as claimed in claim 6, wherein when the compound of formula I comprises an enantiomeric form, said process further comprising at least one of the following steps:

forming a salt of said compound with an enantiomerically pure acid or base, or chromatographing said compound on a chiral stationary phase, or derivatizating said compound with a chiral enantiomerically pure compound, and separating diastereomers thus obtained, and removing chiral auxiliary groups.

9. The process as claimed in claim 6, further comprising the step of:

isolating the compound of formula I in free form.

10. The process as claimed in claim 6, further comprising the step of:

converting the compound of formula I into at least one physiologically tolerable salt.

11. A process for preparing a compound of formula I, as described in claim 1, comprising the steps of:

reacting an aminophosphinic or -phosphonic acid ester of formula V

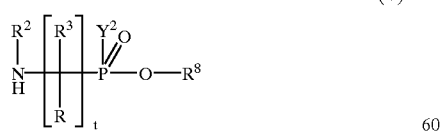

(V)

in which $R^2$, R, $R^3$, t, and $Y^2$ are as defined in formula I and $R^8$ is a hydrogen atom, $(C_1$–$C_6)$-alkyl, phenyl, or benzyl, wherein said alkyl, phenyl, or benzyl is independently unsubstituted or substituted, with a sulfonic acid or carbonyl derivative of formula IV

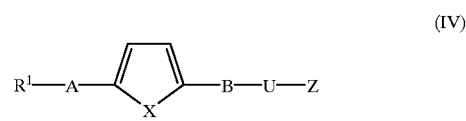

(IV)

in which $R^1$, A, X, U, and B are as defined in formula I, and Z is a halogen atom, imidazolyl, or —$OR^8$, in which $R^8$ is a hydrogen atom, $(C^1$–$C_6)$-alkyl, phenyl, or benzyl, wherein said alkyl, phenyl, or benzyl is independently unsubstituted or substituted, to give a compound of formula VI

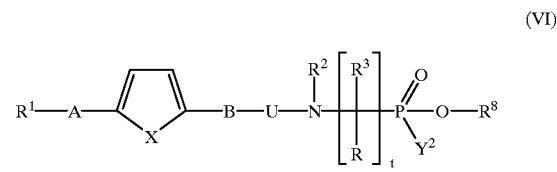

(VI)

and converting the compound of formula VI with removal of the radical $R^8$ into a compound of formula I.

12. The process as claimed in claim 11 wherein when said compound of formula I occurs in enantiomeric form, said process further comprising at least one of the following steps:

forming a salt of said compound with an enantiomerically pure acid or base, or chromatographing said compound on a chiral stationary phase, or derivatizating said compound with a chiral enantiomerically pure compound, and separating diastereomers thus obtained, and removing chiral auxiliary groups.

13. The process as claimed in claim 11, further comprising the step of:

isolating the compound of formula I in free form.

14. The process as claimed in claim 11, further comprising the step of:

converting said compound of formula I into at least one physiologically tolerable salt.

15. A process for preparing a compound of formula I, as described in claim 1, comprising the steps of, reacting a compound of formula VII

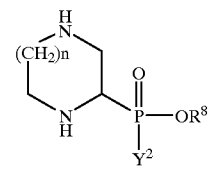

(VII)

where n is the integer zero, 1, or 2, $Y^2$ is as defined under G. in claim 1, and $R^8$ is a hydrogen atom, $(C_1$–$C_6)$-alkyl, phenyl, or benzyl, wherein said alkyl, phenyl, or benzyl is independently unsubstituted or substituted, with the aid of a protective group E to give a compound of formula VIII,

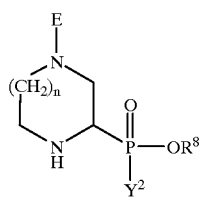

(VIII)

reacting the compound of formula VIII with a compound of formula IV

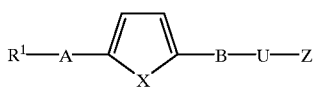

(IV)

in which $R^1$, A, X, U, and B are as defined in formula I and Z is a halogen atom, imidazolyl, or —$OR^8$, in which $R^8$ is a hydrogen atom, ($C_1$–$C_6$)-alkyl, phenyl, or benzyl, wherein said alkyl, phenyl, or benzyl is independently unsubstituted or substituted, to yield a compound of formula IX

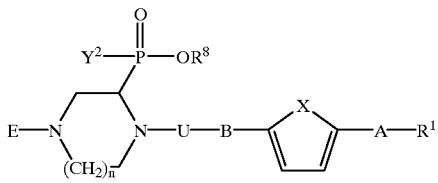

(IX)

and then converting the compound of formula IX, with removal of the protective group E and of the radical $R^8$, into the compound of formula I.

16. The process as claimed in claim 15, wherein when said compound of formula I occurs in enantiomeric form, said process further comprising at least one of the following steps:

forming a salt of said compound with an enantiomerically pure acid or base, or chromatographing said compound on a chiral stationary phase, or derivatizating said compound with a chiral enantiomerically pure compound, and separating diastereomers thus obtained, and removing chiral auxiliary groups.

17. The process as claimed in claim 15, further comprising the step of:

isolating the compound of formula I in free form.

18. The process as claimed in claim 15, further comprising the step of:

converting the compound of formula I into at least one physiologically tolerable salt.

19. A pharmaceutical composition for prophylaxis or therapy of a disorder in a human or animal patient, said disorder involving, at least in part, an increased activity of matrix-degrading metalloproteinase, comprising an amount efficacious for said prophylaxis or therapy, of at least one compound of formula I, a stereoisomeric form thereof, a physiologically tolerable salt thereof, or a mixture of any of the foregoing, together with at least one pharmaceutically suitable and physiologically tolerable excipient; said compound of formula I being:

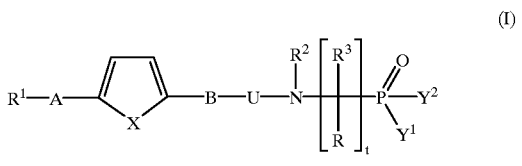

(I)

a stereoisomeric form thereof, or a physiologically tolerable salt thereof, where (A.) $R^1$ is
1. phenyl;
2. phenyl, which is mono- or disubstituted by
  2.1. ($C_1$–$C_6$)-alkyl,
  2.2. hydroxyl,
  2.3. ($C_1$–$C_6$)-alkyl-C(O)—O—,
  2.4. ($C_1$–$C_6$)-alkyl-O—,
  2.5. ($C_1$–$C_6$)-alkyl-O-($C_1$–$C_4$)-alkyl-O—,
  2.6. halogen,
  2.7. —$CF_3$,
  2.8. —CN,
  2.9. —$NO_2$,
  2.10. HO—C(O)—,
  2.11. ($C_1$–$C_6$)-alkyl-O—C(O)—,
  2.12. methylenedioxo,
  2.13. $R^4$—($R^5$)N—C(O)—,
  2.14. $R^4$—($R^5$)N—, or
  2.15. a residue described under A.3.1 to A.3.16;
3. a residue described under A.3.1 to A.3.16, which is unsubstituted or substituted by one or more radicals described under A.2.1 to A.2.15,
  3.1. pyrrole,
  3.2. pyrazole,
  3.3. imidazole,
  3.4. triazole,
  3.5. thiophene,
  3.6. thiazole,
  3.7. oxazole,
  3.8. isoxazole,
  3.9. pyridine,
  3.10. pyrimidine,
  3.11. pyrrolidine,
  3.12. indole,
  3.13. benzothiophene,
  3.14. benzimidazole,
  3.15. benzoxazole, or
  3.16. benzothiazole; or
4. —O-($C_1$–$C_6$)-alkyl;

(B1.) $R^2$ is
1. a hydrogen atom;
2. ($C_1$–$C_6$)-alkyl-;
3. phenyl-$(CH_2)_n$—, in which phenyl is unsubstituted or mono-or disubstuted with radicals described under A.2.1 to A.2.15, or is substituted by —NH—C(O)-($C_1$–$C_3$)-alkyl, and n is the integer zero, 1, or 2; or
4. picolyl;

(B2.) $R^4$ and $R^5$ independently of one another are identical or different and are
1. a hydrogen atom;
2. ($C_1$–$C_6$)-alkyl-;
3. HO—C(O)-($C_1$–$C_6$)-alkyl-;
4. phenyl-$(CH_2)_n$—, in which phenyl is unsubstituted or mono- or disubstituted with radicals described under A.2.1 to A.2.15, or is substituted by —NH—C(O)-($C_1$–$C_3$)-alkyl, and n is the integer zero, 1, or 2;
5. picolyl; or
6. $R^4$ and $R^5$, together with the nitrogen to which they are bonded, form a 4- to 7-membered ring, and the ring is unsubstituted, or a carbon atom in the ring is replaced by —O—, —S—, or —NH—, or two adjacent carbon atoms of the 4- to 7-membered ring are part of a benzyl radical;

(C.) R and $R^3$ are identical or different and are
1. a hydrogen atom;
2. ($C_1$–$C_{10}$)-alkyl-, in which alkyl is unsubstituted or monosubstituted by —OH;
3. ($C_2$–$C_{10}$)-alkenyl-, in which alkenyl is linear or branched;
4. $R^2$—O-($C_1$–$C_6$)-alkyl-;
5. $R^2$—S(O)$_n$-($C_1$–$C_6$)-alkyl-, where n is the integer zero, 1, or 2;
6. $R^2$—S(O)(=NH)-($C_1$–$C_6$)-alkyl-;
7. a radical of formula IIo $$\underset{W}{\underset{|}{(CH_2)_n}}\!\!\!\!\!\!\!\overset{N}{\overset{||}{\diagup}}\!\!\!\!\!\!\!-S-(C_1-C_6)-Alkyl- \qquad (IIo)$$

in which n is the integer zero, 1, or 2, and W is a nitrogen, oxygen, or sulfur atom;
8. phenyl-($CH_2$)$_m$—, in which m is the integer zero, 1, 2, 3, 4, 5, or 6, wherein the —($CH_2$)$_m$— chain is unsubstituted or monosubstituted by —OH, and wherein phenyl is unsubstituted or mono- or disubstituted by
   8.1 radicals described under A.2.1 to A.2.15,
   8.2 —O—($CH_2$)$_m$-phenyl, in which phenyl is unsubstituted or mono- or disubstituted with radicals described under A.2.1 to A.2.15, and m is the integer zero, 1, 2, 3, 4, 5, or 6,
   8.3 —C(O)—($CH_2$)$_m$-phenyl, in which phenyl is defined under C.8.2;
9. residue-($CH_2$)$_m$—, in which residue is defined under A.3.1 to A.3.16, m is defined under C.8, the —($CH_2$)$_m$— chain is unsubstituted or monosubstituted by —OH, and residue is unsubstituted or mono- or disubstituted by
   9.1 radicals described under A.2.1 to A.2.15,
   9.2 —CH(O),
   9.3 —SO$_2$-phenyl, in which phenyl is unsubstituted or substituted as defined under C.8.2 or C.8.3,
   9.4 —O—($CH_2$)$_m$-phenyl;
10. —($CH_2$)$_m$—P(O)(OH)-($C_1$–$C_3$)-alkyl, in which m is defined under C.8;
11. a characteristic radical of an amino acid;
12. $R^6$—C(O)-($C_0$–$C_6$)-alkyl- in which $R^6$ is
   12.1. a hydrogen atom,
   12.2. ($C_1$–$C_6$)-alkyl-,
   12.3. phenyl, which is unsubstituted or substituted with one or more radicals described under A.2.1 to A.2.15,
   12.4. residue, which is defined under A.3.1 to A.3.16, and is unsubstituted or substituted with one or more radicals described under A.2.1 to A.2.15, or is substituted by -($C_1$–$C_4$)-alkyl-COOH,
   12.5. —OH,
   12.6. —OR$^2$, in which $R^2$ has the meaning described under B1.1 to B1.4,
   12.7. —NR$^4$—(R$^5$), in which $R^4$ and $R^5$ are defined under B2.1 to B2.6,
   12.8. residue-($CH_2$)—NH—, in which residue is defined under A.3.1 to A.3.16, and is unsubstituted or substituted with one or more radicals described under A.2.1 to A.2.15, and m is defined under C.8,
   12.9. $R^4$—(R$^5$)N—NH—, in which $R^4$ and $R^5$ are defined under B2.1 to B2.6,
   12.10. HO—C(O)—CH($R^3$)—NH—, in which $R^3$ is defined under C.1 to C.11;
13. —($CH_2$)$_p$—N($R^9$)($R^{10}$), in which p is an integer zero, 1, 2, 3, or 4, in which $R^9$ and $R^{10}$ are identical or different and are
   13.1 a hydrogen atom,
   13.2. phenyl-($CH_2$)$_m$—, in which phenyl is unsubstituted or mono- or disubstituted with radicals described under A.2.1 to A.2.15, and m is the integer zero, 1, 2, or 3,
   13.3. $R^x$—C(O)—, in which $R^x$ is
      3.1 ($C_1$–$C_6$)-alkyl-,
      3.2 ($C_2$–$C_6$)-alkenyl-,
      3.3 phenyl-($CH_2$)$_m$—, in which phenyl is unsubstituted or mono- or disubstituted with radicals described under A.2.1 to A.2.15, and m is the integer zero, 1, 2, or 3, or
      3.4 residue-($CH_2$)$_m$—, in which residue is defined under A.3.1 to A.3.16,
   13.4. $R^x$—O—C(O)—, in which $R^x$ is defined under C.13.3,
   13.5. $R^x$—CH(NH$_2$)—C(O)—, in which $R^x$ is defined under C.13.3,
   13.6. $R^8$—N($R^7$)—C(O)—, in which $R^8$ is
      6.1 a hydrogen atom
      6.2 ($C_1$–$C_6$)-alkyl-,
      6.3 phenyl-($CH_2$)$_m$, in which phenyl is unsubstituted or mono- or disubstituted with radicals described under A.2.1 to A.2.15, and m is the integer zero, 1, 2, or 3, or
      6.4 residue-($CH_2$)$_m$, in which residue is defined under A.3.1 to A.3.16, and is unsubstituted or substituted with one or more radicals described under A.2.1 to A.2.15, m is the integer zero, 1, 2, or 3, and in which $R^7$ is a hydrogen atom or ($C_1$–$C_6$)-alkyl-, or in which $R^7$ and $R^8$, together with the nitrogen atom to which they are bonded, form a 4- to 7-membered ring, and the ring is unsubstituted or a carbon atom in the ring is replaced by —O—, —S—, or —NH—,
   13.7. $R^x$—SO$_2$—, in which $R^x$ is defined under C.13.3,
   13.8. $R^x$—NH—C(=NR$^7$)—, in which $R^x$ is defined under C.13.3 and $R^7$ is defined under C.13.6.4, or $R^x$ and $R^7$ are
      8.1 ($C_1$–$C_6$)-alkyl-C(O)—,
      8.2 —NO$_2$ or
      8.3 —SO$_2$—($CH_2$)$_q$-phenyl, in which phenyl is unsubstituted or mono- or disubstituted with radicals described under A.2.11 to A.2.15, and q is the integer zero, 1, 2, or 3,
   13.9. —SO$_2$—($CH_2$)$_q$-phenyl-phenyl, in which each phenyl independently is unsubstituted or mono- or disubstituted with radicals described under A.2.1 to A.2.15, and q is the integer zero, 1, 2, or 3, or 13.10. a radical of formula IIp

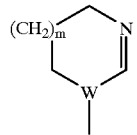 (IIp)

in which m is the integer zero, 1, 2, or 3, and W is a nitrogen atom or sulfur atom, or $R^9$ and $R^{10}$, together with the nitrogen atom to which they are bonded, form a ring chosen from radicals of the subformulae IIa to IIn,

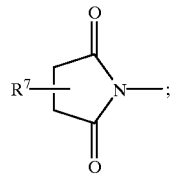 (IIa)

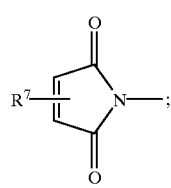 (IIb)

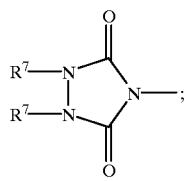 (IIc)

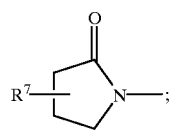 (IId)

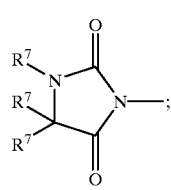 (IIe)

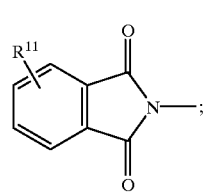 (IIf)

-continued

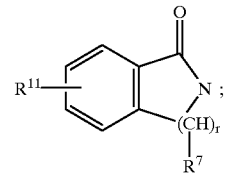 (IIg)

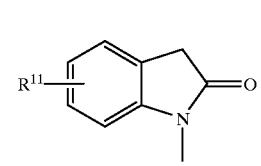 (IIh)

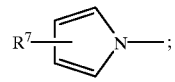 (IIi)

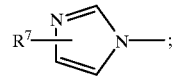 (IIj)

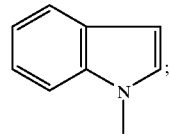 (IIk)

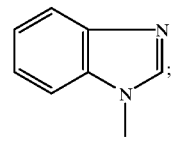 (IIl)

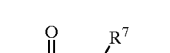

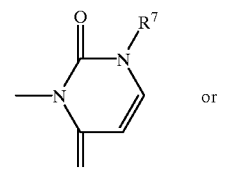 (IIm)

or

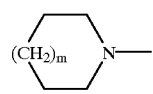 (IIn)

where r is the integer 1 or 2, $R^{11}$ is a radical described under A.2.1 to A.2.15, $R^7$ is defined under C.13.6.4, and m is defined under C.13.2, and a carbon atom in the ring is replaced by zero or one heterospecies chosen from oxygen, sulfur, or nitrogen atom which is unsubstituted or monosubstituted with $R^2$;

14. —OH;

15. =O;

16. $(C_1-C_6)$-alkyl-; or in the compound of formula I, a —C(R)(R³)— radical is optionally replaced by —NH— or —NR²— in which $R^2$ is defined under B1.1 to B1.4;

(D.) t is an integer 1, 2, 3, or 4;

(E.) alternatively, $R^2$ and $R^3$ together form a ring with an exocyclic phosphinic or phosphonic acid radical of the subformula II

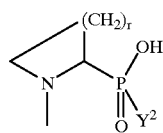

(II)

in which r is the integer zero, 1, 2, or 3, and one carbon atom in the ring of the radical of subformula II is replaced by zero or one heterospecies chosen from —O—, —S—, or —($R^7$)N—, in which $R^7$ is 1. a hydrogen atom;
2. $(C_1-C_6)$-alkyl;
3. phenyl, in which phenyl is unsubstituted or substituted with one or more radicals described under A.2.1 to A.2.15;
4. benzyl, in which benzyl is unsubstituted or substituted with one or more radicals described under A.2.1 to A.2.15; or
5. $R^2N—C(=NH)$— where $R^2$ has the meaning described under B1.1 to B1.4, and the carbon atoms in the ring of the subformula II are unsubstituted or mono- or polysubstituted by $(C_1-C_6)$-alkyl-, phenyl-, phenyl-$(CH_2)_m$— or HO—, or combinations thereof;

(F.) U is —$SO_2$—;

(G.) $Y^1$ is —OH, and $Y^2$ is a) a hydrogen atom;
b) —OH;
c) —$(CH_2)_u$-phenyl, in which u is zero or 1;
d) —O-$(C_1-C_4)$-alkyl, in which alkyl is linear or branched; or
e) —O—$(CH_2)_s$-phenyl, in which s is zero or 1;

(H.) A is a) a covalent bond;
b) —O—;
c) —CH=CH—; or
d) —C≡C—;

(I.) B is a) —$(CH_2)_m$—, in which m is defined under C.13.2;
b) —O—$(CH_2)_p$, in which p is an integer from 1 to 5; or
c) —CH=CH—; and (J.) X is —CH=CH—.

20. A method for the prophylaxis or treatment of a disorder in a human or animal patient, involving, at least in part, an increased activity of at least one matrix-degrading metalloproteinase, said method comprising the step of administering to said patient an amount, efficiacious for said prophylaxis or therapy, of a compound of formula I as claimed in claim 1, a stereoisomeric form thereof, or a physiologically tolerable salt thereof, or a combination of any of the foregoing.

21. The method as claimed in claim 20, wherein said disorder is a degenerative joint disorder, chondrolysis after joint trauma, joint immobilization, or a torn ligament, a disorder of the connective tissue, a periodontal disorder, a wound healing disorder, a chronic disorder of the locomotory apparatus, an arthropathy, a myalgia, a disorder of the bone metabolism, ulceration, atherosclerosis, stenosis, an inflammation, a carcinomatous disorder, tumor metastasis formation, cachexia, anorexia or septic shock.

22. The method as claimed in claim 20, wherein said disorder is osterorathrosis, spondylosis, collagenosis, or results from joint immobilization after meniscus or patella injury, or an inflammatory, immunologically or metabolically related acute or chronic arthritis.

\* \* \* \* \*

UNITED STATES PATENT AND TRADEMARK OFFICE
CERTIFICATE OF CORRECTION

PATENT NO. : 6,235,727 B1
DATED : May 22, 2001
INVENTOR(S) : Manfred Schudok et al.

It is certified that error appears in the above-identified patent and that said Letters Patent is hereby corrected as shown below:

<u>Title page,</u>
Item [75], Inventors, "Eppstein" should read -- Eppstein/Ts. --.

<u>Column 28,</u>
Line 22, "Phenyl-$(CH_2)_n$–" should read -- phenyl-$(CH_2)_n$– --.

<u>Column 29,</u>
Line 60, "A.2.1 115" should read -- A.2.15 --.

<u>Column 32,</u>
Line 45, in the structure for formula (II), "$y^2$" should read -- $Y^2$ --.

<u>Column 33,</u>
Line 2, after "–OH", insert a comma.

<u>Column 34,</u>
Line 36, "ore more" should read -- or more --.

<u>Column 35,</u>
In the structure for formula (III),

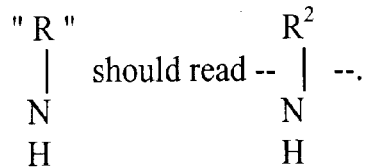

<u>Column 36,</u>
Line 10, "$(C^1$–$C_6)$-alkyl" should read -- $(C_1$–$C_6)$-alkyl --.
Line 49, "steps of," should read -- steps of: --.

<u>Column 38,</u>
Line 56, "mono-or disubstuted" should read -- mono- or disubstituted --.

UNITED STATES PATENT AND TRADEMARK OFFICE
CERTIFICATE OF CORRECTION

PATENT NO. : 6,235,727 B1
DATED : May 22, 2001
INVENTOR(S) : Manfred Schudok et al.

It is certified that error appears in the above-identified patent and that said Letters Patent is hereby corrected as shown below:

Column 40,
Line 62, "A.2.11" should read -- A.2.1 --.

Column 44,
Line 26, "tom ligament" should read -- torn ligament --.

Signed and Sealed this

Eighth Day of October, 2002

Attest:

JAMES E. ROGAN
Attesting Officer
Director of the United States Patent and Trademark Office